US012187692B2

United States Patent
Karpov et al.

(10) Patent No.: US 12,187,692 B2
(45) Date of Patent: Jan. 7, 2025

(54) PROCESS FOR PRODUCING ETHYLENE OXIDE BY GAS-PHASE OXIDATION OF ETHYLENE

(71) Applicant: BASF SE, Ludwigshafen am Rhein (DE)

(72) Inventors: Andrey Karpov, Ludwigshafen am Rhein (DE); Marco Oskar Kennema, Ludwigshafen am Rhein (DE); Nicolas Duyckaerts, Ludwigshafen am Rhein (DE); Christian Walsdorff, Ludwigshafen am Rhein (DE); Christian Bartosch, Ludwigshafen am Rhein (DE); Juergen Zuehlke, Ludwigshafen am Rhein (DE); Miguel Angel Romero Valle, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 888 days.

(21) Appl. No.: 17/285,780

(22) PCT Filed: Sep. 19, 2019

(86) PCT No.: PCT/EP2019/075188
§ 371 (c)(1),
(2) Date: Apr. 15, 2021

(87) PCT Pub. No.: WO2020/078658
PCT Pub. Date: Apr. 23, 2020

(65) Prior Publication Data
US 2021/0387958 A1    Dec. 16, 2021

(30) Foreign Application Priority Data
Oct. 15, 2018   (EP) ..................... 18200481

(51) Int. Cl.
*C07D 301/10* (2006.01)
*B01J 21/04* (2006.01)
(Continued)

(52) U.S. Cl.
CPC ............ *C07D 301/10* (2013.01); *B01J 21/04* (2013.01); *B01J 23/688* (2013.01); *B01J 35/31* (2024.01);
(Continued)

(58) Field of Classification Search
CPC ....... C07D 301/10; B01J 35/695; B01J 35/31; B01J 35/633; B01J 35/612; B01J 35/40; B01J 35/56; B01J 21/04; B01J 23/688
See application file for complete search history.

(56) References Cited

U.S. PATENT DOCUMENTS

| 4,356,312 | A | 10/1982 | Nielsen et al. |
| 4,731,350 | A | 3/1988 | Boxhoorn et al. |

(Continued)

FOREIGN PATENT DOCUMENTS

| CN | 102688784 A | 9/2012 |
| DE | 2300512 A1 | 7/1973 |

(Continued)

OTHER PUBLICATIONS

International Preliminary Report on Patentability received for PCT Patent Application No. PCT/EP2019/075188, mailed on Feb. 10, 2021, 12 pages.

(Continued)

*Primary Examiner* — Clinton A Brooks
*Assistant Examiner* — Jerica Katlynn Wilson
(74) *Attorney, Agent, or Firm* — Faegre Drinker Biddle & Reath LLP

(57) ABSTRACT

A process for producing ethylene oxide by gas-phase oxidation of ethylene, comprising: directing a feed comprising
(Continued)

gaseous ethylene and gaseous oxygen through a packing of individual shaped catalyst bodies, under conditions conducive to obtain a reaction mixture containing at least 2.7 vol.-% of ethylene oxide, wherein each shaped catalyst body comprises silver deposited on a refractory support and is characterized by a content of at least 20 wt.-% of silver, relative to the total weight of the shaped catalyst body; a BET surface area in the range of 1.6 to 3.0 $m^2/g$; a first face side surface, a second face side surface and a circumferential surface with a plurality of passageways extending from the first face side surface to the second face side surface; and a uniform multilobed cross-section; and a longest direct diffusion pathway d, with 2d being in the range of 0.7 to 2.4 mm, wherein the longest diffusion pathway d is defined as the shortest distance from the geometric surface of the shaped catalyst body to a point inside the structure of the shaped catalyst body for which point the shortest distance is the largest among all points. The process allows for increased activity and/or stability of the catalyst while maintaining or increasing selectivity at high productivity.

14 Claims, 8 Drawing Sheets

(51) Int. Cl.
| | | |
|---|---|---|
| *B01J 23/68* | (2006.01) | |
| *B01J 35/31* | (2024.01) | |
| *B01J 35/40* | (2024.01) | |
| *B01J 35/56* | (2024.01) | |
| *B01J 35/61* | (2024.01) | |
| *B01J 35/63* | (2024.01) | |
| *B01J 35/66* | (2024.01) | |

(52) U.S. Cl.
CPC .............. *B01J 35/40* (2024.01); *B01J 35/56* (2024.01); *B01J 35/612* (2024.01); *B01J 35/633* (2024.01); *B01J 35/695* (2024.01)

(56) References Cited

U.S. PATENT DOCUMENTS

| | | |
|---|---|---|
| 4,837,194 A | 6/1989 | Hayden |
| 4,908,343 A | 3/1990 | Bhasin |
| 4,921,681 A | 5/1990 | Ozero et al. |
| 5,187,140 A | 2/1993 | Thorsteinson et al. |
| 5,504,052 A | 4/1996 | Rizkalla et al. |
| 5,504,053 A | 4/1996 | Chou et al. |
| 5,646,087 A | 7/1997 | Rizkalla et al. |
| 6,452,027 B1 | 9/2002 | Billig et al. |
| 7,553,795 B2 | 6/2009 | Bortinger et al. |
| 8,378,129 B2 | 2/2013 | Bhise et al. |
| 8,546,297 B2 | 10/2013 | Rokicki et al. |
| 2014/0187417 A1 | 7/2014 | Pak |
| 2015/0045565 A1* | 2/2015 | Richard et al. ......... C07C 41/03 |
| 2015/0119590 A1 | 4/2015 | Li et al. |
| 2018/0021755 A1 | 1/2018 | Suchanek |

FOREIGN PATENT DOCUMENTS

| | | |
|---|---|---|
| DE | 2454972 A1 | 6/1975 |
| DE | 2521906 A1 | 12/1975 |
| DE | 3414717 A1 | 10/1985 |
| EP | 0014457 A2 | 8/1980 |
| EP | 0082609 A1 | 6/1983 |
| EP | 0085237 A1 | 8/1983 |
| EP | 0172565 A2 | 2/1986 |
| EP | 0266015 A1 | 5/1988 |
| EP | 0339748 A2 | 11/1989 |
| EP | 0357293 A1 | 3/1990 |
| EP | 0716884 A2 | 6/1996 |
| EP | 0902726 A1 | 3/1999 |
| EP | 1115486 A1 | 7/2001 |
| EP | 1478458 A1 | 11/2004 |
| EP | 1613428 A2 | 1/2006 |
| EP | 1675678 A1 | 7/2006 |
| EP | 1893331 A1 | 3/2008 |
| EP | 3254756 A1 | 12/2017 |
| WO | 2004/014549 A1 | 2/2004 |
| WO | 2004/094055 A2 | 11/2004 |
| WO | 2004/101144 A1 | 11/2004 |
| WO | 2006/102189 A1 | 9/2006 |
| WO | 2007/021472 A2 | 2/2007 |
| WO | 2008/054654 A2 | 5/2008 |
| WO | 2009/029414 A1 | 3/2009 |
| WO | 2009/029419 A1 | 3/2009 |
| WO | 2009/114411 A2 | 9/2009 |
| WO | 2010/008920 A2 | 1/2010 |
| WO | 2011/153390 A2 | 12/2011 |
| WO | 2012/091898 A2 | 7/2012 |
| WO | 2012/140614 A1 | 10/2012 |
| WO | 2012/143557 A1 | 10/2012 |
| WO | 2012/143559 A1 | 10/2012 |
| WO | 2013/066557 A1 | 5/2013 |
| WO | 2013/077839 A1 | 5/2013 |
| WO | 2014/105770 A1 | 7/2014 |
| WO | 2015/095508 A1 | 6/2015 |
| WO | WO-2018029189 A1 * | 2/2018 ............ B01J 23/002 |
| WO | 2018/044992 A1 | 3/2018 |

OTHER PUBLICATIONS

International Search Report and Written Opinion received for PCT Patent Application No. PCT/EP2019/075188, mailed on Nov. 19, 2019, 11 pages.

* cited by examiner

PROCESS FOR PRODUCING ETHYLENE OXIDE BY GAS-PHASE OXIDATION OF ETHYLENE

CROSS-REFERENCE TO RELATED APPLICATIONS

This application is a national stage application (under 35 U.S.C. § 371) of PCT/EP2019/075188, filed Sep. 19, 2019, which claims benefit of European Application No. 18200481.2, filed Oct. 15, 2018, both of which are incorporated herein by reference in their entirety.

The present invention relates to a process for producing ethylene oxide by gas-phase oxidation of ethylene.

Ethylene oxide is produced in large quantities and is primarily used as an intermediate in the production of several industrial chemicals. In the industrial oxidation of ethylene to ethylene oxide, heterogeneous catalysts comprising silver are used. To carry out the heterogeneously catalyzed gas-phase oxidation, a mixture of an oxygen-comprising gas, such as air or pure oxygen, and ethylene is generally passed through a plurality of tubes which are arranged in a reactor in which a packing of shaped catalyst bodies is present.

Catalyst performance is characterized by conversion, selectivity, activity, longevity of catalyst activity, and mechanical stability. Moreover, the performance in the reactor tubes is characterized by the packed density of the catalyst in the volume of the tubes and pressure drop across the catalyst bed. For instance, "conversion" has been defined as the percentage of ethylene or oxygen fed to the reactor which undergoes reaction. Selectivity is the molar fraction of the converted ethylene yielding the desired ethylene oxide. The product of the ethylene oxide selectivity and the ethylene conversion is equal to the ethylene oxide yield, or the percentage of the ethylene feed that is converted into ethylene oxide.

The "activity" is generally expressed in terms of weight of ethylene oxide produced per volume of catalyst per hour at specified reaction conditions and rate of feeds. The lower the activity of a reaction system, the less product produced in a unit time for a given feed rate, reactor temperature, catalyst bed volume or weight, surface area, et cetera. If the activity of a reaction system is low, the commercial value of that system will be low. A low activity can render even a high selectivity process commercially impractical. Activity and selectivity may be also discussed in terms of space-time-yield.

In some instances, activity is measured over a period of time in terms of the amount of alkylene oxide produced at a specified constant temperature. Alternatively, activity may be measured as a function of the temperature required to sustain production of a specified constant amount of alkylene oxide. The useful life of a reaction system is the length of time that reactants can be passed through the reaction system during which acceptable activity or selectivity is observed.

Deactivation refers to a permanent loss of activity, i.e., a decrease in activity which cannot be recovered. As noted above, activity can be increased by raising the temperature, but the need to operate at a higher temperature to maintain a particular activity is representative of deactivation. Furthermore, catalysts tend to deactivate more rapidly when reaction is carried out at higher temperatures.

To be considered satisfactory, a catalyst must not only have a sufficient activity and the catalytic system provide an acceptable selectivity, but the catalyst must also demonstrate a minimum useful life or stability. When a catalyst is spent, typically the reactor must be shut down and partially dismantled to remove the spent catalyst. This results in losses in time and productivity. In addition, the catalyst must be replaced and the silver recovered or, where possible, regenerated.

Even small improvements in activity and selectivity, and the maintenance of activity and selectivity over longer time yield huge dividends in terms of process efficiency.

Catalysts containing high level of silver, such as, e.g., at least 20 wt.-% of silver, are often able to increase the activity and/or stability of the catalyst, as compared to a similar catalyst not having the same high silver concentration. U.S. Pat. No. 5,187,140 discloses catalysts for the epoxidation of ethylene, which catalysts contain a high silver content on carriers having a high surface area and a high pore volume. Unfortunately, increased silver contents, while increasing catalyst activity, may result in selectivity losses.

For economical purposes, it is preferred to operate production plants for olefin oxide at maximum productivity and highest selectivity. In order to maximize the productivity, the catalyst work rate has to be increased which is usually achieved by either raising the flow rate, i.e., Gas Hourly Space Velocity (GHSV), at fixed olefin oxide concentration at the reactor outlet and/or changing the concentration of the olefin oxide in the reactor outlet by adjusting the olefin and oxygen conversion. The most common procedure to increase the productivity is the adjustment of the olefin oxide concentration in the reactor outlet. In general, the outlet concentration adjustments are achieved by increasing the catalyst temperature and thereby increasing the olefin and oxygen conversion. However, by increasing the level of olefin oxide in the reactor outlet, the selectivity of the process decreases significantly which counteracts the desired productivity increasing.

Accordingly, catalysts are sought which can exhibit not only enhanced activity but also maintained or increased selectivity. One possibility to influence selectivity resides in variation of the geometrical shape of catalyst bodies.

WO 2012/091898 A2 describes a catalyst useful for the epoxidation of olefins comprising a carrier with at least three lobes having a contoured shape and a plurality of passageways.

US 2015/0119590 A1 describes silver catalysts suitable for producing ethylene oxide by oxidation of ethylene, comprising α-alumina supports in the form of five-hole cylinder bodies.

U.S. Pat. No. 4,837,194 describes catalysts for the production of alkylene oxides comprising an α-alumina support in the form of cylinders pierced by seven longitudinal holes.

WO 2009/114411 A2 describes a geometrically shaped solid carrier for epoxidizing an olefin having thin walls of preferably less than 2.5 mm.

CN 102688784 A describes an alumina support for a silver catalyst suitable for olefin epoxidation, comprising a cylindrical substrate with a central passage, wherein the alumina support further comprises at least three partially cylindrical leaflets.

It is an object of the present invention to provide a high productivity process for producing ethylene oxide allowing for increased activity and/or stability of the catalyst while maintaining or increasing selectivity.

The object is achieved by providing a process for producing ethylene oxide by gas-phase oxidation of ethylene, comprising directing a feed comprising gaseous ethylene and gaseous oxygen through a packing of individual shaped catalyst bodies, under conditions conducive to obtain a reaction mixture containing at least 2.7 vol.-% of ethylene oxide, wherein each shaped catalyst body comprises silver deposited on a refractory support and is characterized by a content of at least 20 wt.-% of silver, relative to the total weight of the shaped catalyst body; and a BET surface area in the range of 1.6 to 3.0 m²/g.

In an embodiment, each shaped catalyst body is characterized by a longest direct diffusion pathway d, with 2d being in the range of 0.7 to 2.4 mm, wherein the longest diffusion pathway d is defined as the shortest distance from the geometric surface of the shaped catalyst body to a point inside the structure of the shaped catalyst body for which point the shortest distance is the largest among all points.

In an embodiment, each shaped catalyst body is characterized by a first face side surface, a second face side surface and a circumferential surface with a plurality of passageways extending from the first face side surface to the second face side surface; and a uniform multilobed cross-section.

The shaped catalyst body may be defined by a longest direct diffusion pathway d, with 2d (2d is also referred to as "thickness") being in the range of 0.7 to 2.4, preferably 0.7 to 2.2 mm, 0.7 to 2.1 mm or 0.7 to 2.0 mm, more preferably 0.8 to 2.4 mm, 0.8 to 2.2 mm, 0.8 to 2.1 mm or 0.8 to 1.8 mm, even more preferably 1.4 to 2.4 mm, such as 1.7 to 2.2 mm or 1.8 to 2.1 mm, wherein the longest direct diffusion pathway d is defined as a distance twice the shortest distance from the geometric surface of the shaped catalyst body to a point inside the structure of the shaped catalyst body for which point the shortest distance is the largest among all points. It is understood that the longest direct diffusion pathway is a strictly geometric term. The actual diffusion pathway of a reactant species and/or product species is typically much longer than the straight pathway as the species travels through convoluted pore spaces.

The shaped catalyst body has a uniform multilobed cross-section, i.e. a multifoiled ("cloverleaf fashion") cross-section having, e.g., a trefoil, quatrefoil or cinquefoil outer shape. The shaped catalyst body is thus characterized by a multilobe shape, which is meant to denote a cylinder structure which has a plurality of void spaces, e.g., grooves or furrows, running in the cylinder periphery along the cylinder height. Generally, the void spaces are arranged essentially equidistantly around the circumference of the cylinder.

Without wishing to be bound by theory, it is believed that while ethylene usually passes into and out of the catalyst pores easily, the diffusion of the more bulky ethylene oxide takes significantly longer. Under the thus prolonged exposure, ethylene oxide may undergo undesired consecutive reactions induced by the catalyst, which reduces the overall selectivity of the process.

By virtue of their unique shape, the shaped catalyst bodies used in the inventive process have a defined thickness. In order to allow for a quick diffusion of ethylene oxide, it is favorable to provide a shaped catalyst body wherein the pore volume is located predominantly close to the geometric surface of the shaped catalyst body, allowing ethylene oxide to pass out of the pores more quickly and avoiding long diffusion pathways within the catalyst body. The geometric surface of a shaped catalyst body is defined by the external, macroscopic dimensions of the shaped catalyst body taking into account the cross-sectional area, the height and the number of internal passageways, if any. Internal passageways are macroscopic holes or conduits extending through the catalyst bodies, generally having diameters of more than 0.1 mm.

Herein, thickness is defined as a distance twice the longest direct diffusion pathway d which is the shortest distance from the geometric surface (or "outer surface") of the shaped catalyst body to a point inside the structure of the shaped catalyst body for which point the shortest distance is the largest among all points. Thus, the longest direct diffusion pathway d is determined by first identifying a point within the bulk volume of the catalyst body which is farthest away from the closest neighboring geometric surface (or, in other words, which is "farthest inside the body"). The shortest distance from the geometric surface to that point is defined as "longest direct diffusion pathway". In this connection, "geometric surface" can be a circumferential surface of the catalyst body or the surface of an internal passageway (which, of course, is fluidly connected to the outside of the catalyst body) through the body, whichever surface is closer.

For example, in a spherical body the point farthest away from the closest neighboring geometric surface is the center of the spherical body. The shortest distance from the center to the geometric surface equals the radius of the spherical body and, hence, twice the radius (or diameter) corresponds to the "thickness" of the spherical body. For a hollow cylinder shaped catalyst (having a height greater than its wall thickness), a point lying on the midline between the circumferential surface and the surface of the center hole (internal passageway), whose distance from the face side surfaces is at least half the wall thickness, is the point farthest away from the closest neighboring geometric surface. Hence the "thickness" generally corresponds to the wall thickness of the hollow cylinder. For a flat hollow cylinder shaped catalyst (having a height smaller than its wall thickness), the "thickness" of the shaped catalyst body corresponds to its height.

For catalyst bodies having a plurality of internal passageways, wall thickness between the passageways, or between the passageways and the circumferential surface of the catalyst bodies needs to be considered, as illustrated in appended FIG. 1.

Limiting the size or thickness of the shaped catalyst bodies usually leads to an increase in the packing density and an increased resistance to the gas flowing through the packing. This causes an increase in the pressure drop which has to be overcome in order to force the reaction gas mixture through the catalyst packing.

Therefore, the shaped catalyst bodies used in the process of the present invention have passageways extending through the solid catalyst.

In case of a hollow cylinder shaped catalyst, limiting the wall thickness is subject to limitations because excessively reducing the thickness of the walls reduces the mechanical stability and crush strength of the catalyst bodies. Catalyst bodies with lower crush strength and higher attrition tend to produce more broken catalyst bodies and more catalyst fines during handling, shipment, and installation into a commercial reactor. These broken catalyst bodies and catalyst fines create increased pressure drop in the commercial reactor tubes during normal operation and are thus unfavorable. Practically, geometries with extremely thin walls are useful only with catalysts of limited porosity, whose mechanical strength is increased due to their low porosity. Such lower porosity would however have a detrimental impact on the rate of the oxidation.

The shaped catalyst bodies have a first face side surface, a second face side surface and a circumferential surface with a plurality of passageways extending from the first face side surface to the second face side surface. As they display a large free surface area in their cross-section, the shaped bodies oppose a lower resistance to gas flow, with consequently lower pressure drops.

The shaped catalyst body has a uniform multilobed cross-section. The shaped catalyst body having a uniform multilobed cross-section is characterized by a cylinder structure which has a plurality of void spaces, e.g., grooves or furrows, running in the cylinder periphery along the cylinder height.

An axis parallel to the cylinder height and the first face side surface or the second face side surface, respectively, are essentially perpendicular but may deviate therefrom by an angle of up to 30°, such as up to 10° or 20°.

The passageways of the shaped catalyst body may have any technically feasible geometric form, such as an elliptical, polygonal or pincushion-shaped cross-section. An elliptical cross-section may be chosen among circular and oval shapes, for example. A polygonal cross-section may be chosen among rectangular and square shapes, for example. A pincushion-shaped cross-section is understood to comprise edges bowed inwards, i.e., to the center of the pincushion-shape. A preferred pincushion-shaped cross-section may have the shape of a square with all four edges bowed towards the center of the square.

In one embodiment, the passageways of the shaped catalyst body are arranged in a circular fashion with one passageway being assigned to each lobe, wherein neighboring passageways are arranged essentially equidistantly to each other. Here, the term "in a circular fashion" is understood to mean that the centers of the passageways lie on the circumference of a circle connecting the centers of the passageways.

Preferably, the shaped catalyst body comprises outer passageways arranged around a central passageway with one outer passageway being assigned to each lobe, wherein neighboring outer passageways are arranged essentially equidistantly to each other and the outer passageways are arranged essentially equidistantly to the central passageway.

In this embodiment, neighboring outer passageways are arranged essentially equidistantly to each other, preferably in a circular fashion. Here, the term "in a circular fashion" is understood to mean that the centers of the outer passageways lie on the circumference of a circle connecting the centers of the outer passageways. Likewise, the outer passageways are arranged essentially equidistantly to the central passageway. "Essentially equidistant" is understood to mean equidistant, save for the inevitable fluctuations and deviations inherent to the manufacturing process of the carrier. In general, essentially equidistant means a difference of no more than 10%, preferably no more than 5%, most preferably no more than 3% of the mean distance between neighboring outer passageways or the mean distance between the outer passageways and the central passageway, respectively.

Preferably, the cross-section of the multilobe structure has the shape of a substantially equilateral, equiangular polygon with elliptical segments attached to each side. In this case, the cross-section of the outer passageway assigned to a lobe lies partially within an elliptical segment and partially within the polygon. The term "cross-section" refers to a cross-section perpendicular to the central axis of the cylinder.

Preferably, each elliptical segment is mirror-symmetric with regard to a line running from the center of the polygon through the middle of the polygon side to which the elliptical segment is attached, which line bisects one outer passageway. It is understood that the outer passageway is bisected into two halves of the same area, preferably the same area and shape. In a preferred embodiment, the elliptical segments are circular segments, preferably of essentially identical size.

The elliptical segments preferably traverse the side they are attached to and meet at the corners of the polygon. This yields a multilobe shape having individual lobes and indwelling, apical, interlobular interstices.

In preferred embodiments, the shaped catalyst body has an n-fold rotational symmetry, wherein n is the number of outer passageways. Such an arrangement of passageways allows for an essentially uniform wall thickness, especially when the passageways are located symmetrically in each of the lobes.

Preferably, the cross-sectional area of each of the passageways is independently in the range of 0.5 to 13.0 mm². It is preferable that the central passageway has a somewhat smaller cross-sectional area than the outer passageways. Preferably, the central passageway has a cross-sectional area $a_1$ and the outer passageways each have a cross-sectional area $a_2$, and the ratio of $a_1$ to $a_2$ is in the range of 0.15 to 1.0, preferably in the range of 0.25 to 0.45, or preferably in the range of 0.5 to 0.9 and more preferably in the range of 0.6 to 0.8. It was found that such an arrangement allows for high mechanical stability while limiting wall thickness. Preferably, $a_2$ is identical for each of the outer passageways.

Preferably, the ratio of the total cross-sectional area of the passageways to the cross-sectional area of the shaped catalyst body is in the range of 0.12 to 0.35, more preferably in the range of 0.15 to 0.3. The total cross-sectional area of the passageways is understood to mean the sum of the cross-sectional areas of the passageways. The cross-sectional area of the shaped catalyst body is understood to mean the surface area enclosed by the circumferential line of the face side. The cross-sectional area of the shaped catalyst body includes the cross-sectional areas of the passageways. Accordingly, the ratio of the total cross-sectional area of the passageways to the cross-sectional area of the shaped catalyst body reflects the share of the passageway area of the cross-sectional area of the shaped catalyst body.

In a preferred embodiment, the outer passageways have an elliptical cross-section and the central passageway has a polygonal, pincushion-shaped or elliptical cross-section. Preferably, the outer passageways have an essentially identical cross-section. It is especially preferred that all passageways have an elliptical cross-section, especially a circular cross-section.

In a preferred embodiment, the shaped catalyst body has a uniform trilobed structure with three outer passageways arranged around a central passageway, It is especially preferred that the shaped catalyst body has a 3-fold rotational symmetry. The shape of the central passageway may deviate from the 3-fold rotational symmetry. Preferably, however, the shape of the central passageway is part of the 3-fold rotational symmetry. Thus, it is preferable that the three outer passageways have essentially identical, symmetrical cross-sections, and that they are arranged so that their center points form an equal-sided triangle, at the center of which is arranged a central passageway.

In another preferred embodiment, the shaped catalyst body has a uniform tetralobed structure with four outer passageways arranged around a central passageway. It is especially preferred that the shaped catalyst body has a 4-fold rotational symmetry. The shape of the central passageway may deviate from the 4-fold rotational symmetry. Preferably, however, the shape of the central passageway is part of the 4-fold rotational symmetry. Thus, it is preferable that the four outer passageways have essentially identical, symmetrical cross-sections, and that they are arranged so that their center points form a square, at the center of which is arranged a central passageway.

In an especially preferred embodiment, the passageways have a circular cross-section and are arranged in a quincunx pattern.

In another preferred embodiment, the shaped catalyst body has a uniform pentalobed structure with five outer passageways arranged around a central passageway. It is especially preferred that the shaped catalyst body has a 5-fold rotational symmetry. The shape of the central passageway may deviate from the 5-fold rotational symmetry. Preferably, however, the shape of the central passageway is part of the 5-fold rotational symmetry. Thus, it is preferable that the five outer passageways have essentially identical, symmetrical cross-sections, and that they are arranged so that their center points form an equal-sided pentagon, at the center of which is arranged a central passageway.

Preferably, the shortest distance A between two neighboring passageways, i.e. the wall thickness between two neighboring passageways, is in the range of 0.6 to 1.3 mm, preferably 0.7 to 1.2 mm, more preferably 0.8 to 1.1 mm or 0.7 to 1.0 mm. It is understood that outer passageways are neighbors of the central passageway as well as amongst each other. The shortest distance B between each outer passageway and the circumferential surface, i.e. the wall thickness between each outer passageway and the circumferential surface, is in the range of 1.1 to 1.8 mm, preferably 1.2 to 1.7 mm, more preferably 1.3 to 1.6 mm or 1.4 to 1.7 mm. A minimum wall thickness is provided by the definition of the shortest distances A and B, allowing for a high stability of the shaped catalyst body. Further, a maximum wall thickness is provided so as to avoid long diffusion pathways.

The "thickness", i.e. 2d, as defined herein can also be expressed relatively to the shortest distance A or B, whichever is greater. The expression "max(A,B)" is used to denote the value of A or B, whichever is greater. In this connection, the thickness of the shaped catalyst bodies used in the inventive process is preferably in the range of 1.1 max(A,B) to 1.4 max(A,B) (1.1 to 1.4 times max(A,B)), more preferably 1.15 max(A,B) to 1.35 max(A,B), such as 1.20 max(A,B) to 1.30 max(A,B). In an especially preferred embodiment, the "thickness" of the shaped catalyst body fulfills both the following (i) and (ii): (i) the thickness is in the range of 0.7 to 2.4, preferably 0.7 to 2.2 mm, 0.7 to 2.1 mm or 0.7 to 2.0 mm, especially 0.8 to 2.4 mm, 0.8 to 2.2 mm, 0.8 to 2.1 mm or 0.8 to 1.8 mm even more preferably 1.4 to 2.4 mm, such as 1.7 to 2.2 mm or 1.8 to 2.1 mm; and (ii) the thickness is in the range of 1.1 max(A,B) to 1.4 max(A,B), more preferably 1.15 max(A,B) to 1.35 max(A,B), such as 1.20 max(A,B) to 1.30 max(A,B).

In an embodiment, the shaped catalyst body used in the inventive process is in the shape of a plurality of, for example three to five, preferably four, longitudinally intersecting essentially identical hollow cylinders which form a symmetrical multilobed body, the core of which may be solid or comprise a central passageway.

In case the shaped catalyst body is in the shape of three longitudinally intersecting essentially identical hollow cylinders, the shaped catalyst body is a symmetrical trilobed body. In case the shaped catalyst body is in the shape of four longitudinally intersecting essentially identical hollow cylinders, the shaped catalyst body is a symmetrical tetralobed body. In case the shaped catalyst body is in the shape of five longitudinally intersecting essentially identical hollow cylinders, the shaped catalyst body is a symmetrical pentalobed body.

The term "hollow cylinder" is understood to relate to a three-dimensional body bounded by an outer cylinder and an inner channel, the outer cylinder and the inner channel having the same axis, and two bases perpendicular to the outer cylinder's and inner channel's common axis. The outer cylinders are preferably essentially circular cylinders. The distance between the bases along the axis defines the height of the hollow cylinder. The hollow cylinders are essentially identical and intersect longitudinally, i.e. parallel to the outer cylinder's and inner channel's common axis to form a symmetrical multilobed body in a cloverleaf fashion. The inner channels of the hollow cylinder each form one passageway per lobe of the symmetrical multilobed body.

Depending on the number of intersecting hollow cylinders and the degree of intersection, the intersecting hollow cylinders leave a central cavity bounded by the outer surfaces of the hollow cylinders between their inner junctions. This central cavity or core may be solid ("filled") or comprise a central passageway. The presence or absence of a central passageway, as well as its size and shape, is not necessarily determined by the intersection of the hollow cylinders, but may be chosen according to the embodiments below.

The individual hollow cylinders preferably have an essentially uniform wall thickness, the largest wall thickness being preferably not more than 15% thicker than the smallest wall thickness. The smallest wall thickness is preferably in the range of 1.1 to 2.0 mm, preferably 1.2 to 2.0 mm, more preferably 1.3 to 1.9 mm, such as 1.4 to 1.8 mm or 1.4 to 1.7 mm. The wall thickness of the hollow cylinder is understood to mean the distance between the outer cylinder and the inner channel.

The individual hollow cylinders preferably have an outer diameter of 3.0 to 5.0 mm, more preferably 3.5 to 4.5 mm, such as 3.6 to 4.4 mm, especially 3.7 to 4.3 mm or 3.8 to 4.3 mm.

The multilobe structure has a cross-section perpendicular to the cylinder height with the circumscribed circle diameter $d_{cc}$. "Circumscribed circle" means the smallest circle that completely contains the multilobe cross-section within it. Preferably, the cross-section has a quotient of the diameter of the inscribed circle $d_{ic}$ over the diameter of the circumscribed circle $d_{cc}$ of at most 0.9, preferably in the range of 0.65 to 0.85 and most preferably in the range of 0.7 to 0.8, or 0.65 to 0.8, such as 0.7 to 0.8. "Inscribed circle" means the largest possible circle that can be drawn inside the multilobe cross-section.

A quotient of $d_{ic}$ over $d_{cc}$ in this range allows for a lobe size which balances geometric surface area and mechanical strength.

The circumscribed circle diameter $d_{cc}$ is usually in the range of 5 to 80 mm, preferably 5 to 20 mm and especially 5 to 10 mm, most preferably 8.0 to 9.5 mm such as 8.2 to 9.2 mm. Generally, the quotient of the diameter $d_{cc}$ over the height h of the shaped body is in the range of 0.25 to 2.0, preferably 0.5 to 1.5 and more preferably 0.75 to 1.25, for example 0.80 to 1.20 or most preferably 0.90 to 1.15, such as 1.0 to 1.15. A value of $d_{cc}/h$ in this range allows for especially favorable properties of the shaped catalyst body, in particular with regard to the pressure drop.

The height h of the shaped body (equaling the cylinder height) is understood to mean the distance between the two face sides along the central axis of the cylinder. The cylinder height is preferably in the range of 6 to 12 mm, more preferably in the range of 7 to 11 mm, most preferably in the range of 8.0 to 10.0 mm, such as 8.0 to 9.0 mm.

The shape of the preferred catalyst bodies allows for extending the geometric volume/geometric surface ($SA_{geo}/V_{geo}$) ratios beyond those available in simple cylindrical or spherical forms. The geometric surface area $SA_{geo}$ and the geometric volume $V_{geo}$ is derived from the external, macroscopic dimensions of the shaped catalyst body taking into account the cross-sectional area, the height and the number of internal passageways. In other words, the geometric volume $V_{geo}$ of the catalyst bodies is the volume of a solid multilobe structure having the same outer dimensions, minus the volume occupied by the passageways. Likewise, the geometric surface area $SA_{geo}$ is made up of the circumferential surface, the first and second face side surface and the surface defining the passageways. The first and second face side surface, respectively, is the surface area enclosed by the circumferential line of the face side, minus the cross-sectional areas of the passageways. The surface defining the passageways is the surface area lining the passageways.

Preferably, the quotient of the geometric surface of the shaped catalyst body $SA_{geo}$ over the geometric volume of the shaped catalyst body $V_{geo}$ is at least 1.1 mm$^{-1}$ and at most 10 mm$^{-1}$. Preferably, the quotient of $SA_{geo}$ over $V_{geo}$ is in the range of 1.15 mm$^{-1}$ to 5.0 mm$^{-1}$, more preferably in the range of 1.2 mm$^{-1}$ to 2.0 mm$^{-1}$, most preferably in the range of 1.3 to 1.45, or 1.3 to 1.6 mm$^{-1}$. A quotient of $SA_{geo}$ over $V_{geo}$ in this range makes it possible for a better contact of the reaction gases with the catalyst surface to be obtained, which favors the conversion of the reactants and limits the inner diffusion phenomena, with a resulting increase in reaction selectivity.

The preferred shaped catalyst body has a high mechanical stability. Preferably, the shaped catalyst body has a side crush strength of at least 50 N. The term "side crush strength" refers to the force necessary to break the shaped catalyst body at its weakest pressure point. For the purposes of the present invention, the side crush strength is the force which fractures the shaped catalyst body located between two flat parallel plates, with the height of the cylindrical body parallel to the flat parallel plates.

The BET surface area and the porous nature of the catalyst as determined by mercury porosimetry contribute substantially to the active surface area at which the catalytic reaction takes place. For the internal surfaces of the catalyst body to be utilized effectively, the feed gases must diffuse through the pores to reach the internal surfaces, and the reaction products must diffuse away from those surfaces and out of the catalyst body. The catalytic performance is influenced by the catalyst's pore structure.

The shaped catalyst body is characterized by a BET surface area in the range of 1.6 to 3.0 m$^2$/g, preferably 1.8 to 2.8 m$^2$/g, more preferably 2.0 to 2.6 m$^2$/g, most preferably 2.3 to 2.5 m$^2$/g. The BET method is a standard, well-known method and widely used method in surface science for the measurements of surface areas of solids by physical adsorption of gas molecules. The BET surface is determined according to DIN ISO 9277 herein, unless stated otherwise.

The porosity of the shaped catalyst body may further be characterized by its Hg pore volume. Preferably, the shaped catalyst body has a total Hg pore volume of 0.2 mL/g to 0.6 mL/g, preferably 0.25 mL/g to 0.5 mL/g, especially preferably 0.3 mL/g to 0.4 mL/g, as determined by mercury porosimetry. Mercury porosimetry may be performed using a Micrometrics AutoPore IV 9500 mercury porosimeter (140 degrees contact angle, 485 dynes/cm Hg surface tension, 60000 psia max head pressure). The Hg porosity is determined according to DIN 66133 herein, unless stated otherwise. It is believed that a Hg pore volume in this range allows for a favorable duration of exposure of the obtained ethylene oxide to the catalyst.

Preferably, the shaped catalyst body has a multimodal pore size distribution with at least one pore size distribution maximum in the range of 0.1 to 3.0 µm. Preferably at least 40% of the total Hg pore volume of the shaped catalyst body stems from pores with a diameter in the range of 0.1 to 3.0 µm. More preferably 50% to 90%, in particular 50% to 80% of the total pore volume of the shaped catalyst body stems from pores with a diameter in the range of 0.1 to 3.0 µm. Preferably, the shaped catalyst body further has at least one pore size distribution maximum in the range of 8.0 to 100 µm.

Preferably at most 50% of the total Hg pore volume of the shaped catalyst body stems from pores with a diameter of 8.0 to 100 µm. More preferably 10% to 50%, in particular 20% to 40% of the total Hg pore volume of the shaped catalyst body stems from pores with a diameter of 8.0 to 100 µm. It is believed that such a multimodal pore size distribution is advantageous because it allows to achieve high catalyst selectivity, activity and durability.

Pore size distribution may be further characterized by, e.g., high resolution Computed Tomography (CT), or by Focused Ion Beam (FIB) Tomography or Scanning Electron Microscopy (SEM). Data collected by these methods, including average pore sizes, may differ from the data obtained by mercury porosimetry. Accordingly, different techniques may be used to complement each other and obtain a full picture on the pore structure of a shaped body.

The shaped catalyst body comprises silver deposited on a porous refractory support. The catalysts contain a high concentration of silver, generally at least 20 wt.-%, relative to the total weight of the shaped catalyst body. Preferably the shaped catalyst body has a content of at least 22 wt.-%, more preferably at least 23 wt.-% most preferably at least 25 wt.-%, relative to the total weight of shaped catalyst body.

For example, the catalyst may comprise 20 to 45% wt.-% of silver, relative to the total weight of the shaped catalyst body. A preferred catalyst comprises 22 to 35 wt.-% of silver, more preferably 23 to 30 wt.-% of silver, e.g., 25 to 30 wt.-% relative to the total weight of the shaped catalyst body. A silver content in this range allows for a favorable balance between activity, stability and cost-efficiency of preparing the shaped catalyst body. The content of silver used herein relates to the actual values obtained by analysis of the shaped catalyst body. The actual value may slightly deviate from a target value calculated from the parameters of the catalyst manufacturing process.

The bulk density of a catalyst is typically much higher than the packed density in, e.g., a tubular reactor such as commercially used for the production of ethylene oxide. The packed density of the shaped catalyst bodies is preferably at least 700 g/L, more preferably 750 to 1200 g/L, in particular 800 to 1000 g/L, as measured in a reactor tube with an inner diameter of 39 mm. The silver density per liter of a tubular reactor packed with catalyst in accordance with this invention, i.e. the packed silver density, is often at least 140 g/L, e.g., at least 180 g/L, preferably at least 200 g/L, in particular at least 220 g/L as measured in a reactor tube with an inner diameter of 39 mm. The silver density per liter of a tubular reactor, i.e. the packed silver density, can be calculated by multiplying packed catalyst density by the silver content of the catalyst bodies.

Besides silver, the shaped catalyst body may comprise one or more promoting species. A promoting species denotes a component that provides an improvement in one or more of the catalytic properties of the catalyst when compared to a catalyst not containing said component. The promoting species can be any of those species known in the art that function to improve the catalytic properties of the silver catalyst. Examples of catalytic properties include operability (resistance to runaway), selectivity, activity, turnover and catalyst longevity.

The shaped catalyst body may comprise a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof. In one embodiment, the transition metal promoter(s) is (are) present in a total amount from 150 ppm to 5000 ppm, typically 225 ppm to 4000 ppm, most typically from 300 ppm to 3000 ppm, expressed in terms of metal(s) relative to the total weight of the shaped catalyst body.

Of the transition metal promoters listed, rhenium (Re) is a particularly efficacious promoter for ethylene epoxidation high selectivity catalysts. The rhenium component in the shaped catalyst body can be in any suitable form, but is more typically one or more rhenium-containing compounds (e.g., a rhenium oxide) or complexes.

Preferably, the shaped catalyst body comprises 400 to 2000 ppm by weight of rhenium, relative to the total weight of the shaped catalyst body. It is preferred that the shaped catalyst body comprises 560 to 1700 ppm by weight of rhenium, more preferably 610 to 1500 ppm by weight of rhenium, most preferably 700 to 1400 ppm by weight of rhenium, e.g., 740 to 1300 ppm by weight of rhenium, relative to the total weight of the shaped catalyst body.

In some embodiments, the shaped catalyst body may include a promoting amount of an alkali metal or a mixture of two or more alkali metals. Suitable alkali metal promoters include, for example, lithium, sodium, potassium, rubidium, cesium or combinations thereof. The amount of alkali metal, e.g. potassium, will typically range from 50 ppm to 5000 ppm, more typically from 300 ppm to 2500 ppm, most typically from 500 ppm to 1500 ppm expressed in terms of the alkali metal relative to the total weight of the shaped catalyst body. The amount of alkali metal is determined by the amount of alkali metal contributed by the porous refractory support and the amount of alkali metal contributed by the impregnation solution described below.

Combinations of heavy alkali metals like cesium (Cs) or rubidium (Rb) with light alkali metals like lithium (Li), sodium (Na) and potassium (K) are particularly preferred.

Cesium is an especially preferred alkali metal promotor. Preferably, the shaped catalyst body comprises 260 to 1750 ppm by weight of cesium, relative to the total weight of the shaped catalyst body. It is preferred that the shaped catalyst body comprises 400 to 1500 ppm by weight of cesium, more preferably 530 to 1500 ppm by weight of cesium, most preferably 600 to 1330 ppm by weight of cesium, e.g., 730 to 1330 ppm by weight of cesium, relative to the total weight of the shaped catalyst body.

Preferably the shaped catalyst body contains at least two light alkali metals, selected from sodium, potassium and lithium. Most preferably the shaped catalyst body contains sodium, potassium and lithium.

Preferably, the shaped catalyst body comprises 40 to 1170 ppm by weight of potassium, relative to the total weight of the shaped catalyst body. It is preferred that the shaped catalyst body comprises 100 to 400 ppm by weight of potassium, most preferably 140 to 250 ppm by weight of potassium. The amount of potassium is determined by the amount of potassium contributed by the porous refractory support and the amount of potassium contributed by the impregnation solution described below.

Preferably, the shaped catalyst body comprises 100 to 2000 ppm by weight of lithium, relative to the total weight of the shaped catalyst body. It is preferred that the shaped catalyst body comprises 150 to 1500 ppm by weight of lithium, most preferably 300 to 750 ppm by weight of lithium. The amount of lithium is determined by the amount of lithium contributed by the porous refractory support and the amount of lithium contributed by the impregnation solution described below.

Preferably, the shaped catalyst body comprises 10 to 1000 ppm by weight of sodium, relative to the total weight of the shaped catalyst body. It is preferred that the shaped catalyst body comprises 20 to 500 ppm by weight of sodium, most preferably 30 to 250 ppm by weight of sodium. The amount of sodium is determined by the amount of sodium contributed by the porous refractory support and the amount of sodium contributed by the impregnation solution described below.

The shaped catalyst body may also include a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters can be used in amounts similar to those used for the alkali or transition metal promoters.

The shaped catalyst body may also include a promoting amount of a main group element or a mixture of two or more main group elements. Suitable main group elements include any of the elements in Groups IIIA (boron group) to VIIA (halogen group) of the Periodic Table of the Elements. For example, the shaped catalyst body can include a promoting amount of sulfur, phosphorus, boron, halogen (e.g., fluorine), gallium, or a combination thereof.

The shaped catalyst body may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm). The amount of rare earth metal promoters can be used in amounts similar to those used for the transition metal promoters.

It is understood that the numerical values used herein to describe the catalyst relate to the values obtained by analysis of the shaped catalyst body. The actual value may slightly deviate from a target value calculated from the parameters of the catalyst manufacturing process.

The shaped catalyst body comprises a porous refractory support. Any refractory support known in the art can be used. Suitable examples of refractory supports are described in EP 0902726, EP 1478458, EP 1675678, EP 3254756, WO 2004/101144, WO 2007/021472, WO 2008/054654, WO 2009/029414, WO 2010/008920, WO 2011/153390A1, WO 2012/143557A1, WO 2012/143559A1, WO 2013/077839A1 or US 2018/0021755.

Preferably, the refractory support is an aluminium oxide support. The aluminium oxide support usually comprises a high proportion of $\alpha$-$Al_2O_3$, for example at least 90 percent by weight, preferably at least 95 percent by weight, most preferably at least 97.5 percent by weight, based on the total weight of the support.

A shaped catalyst body useful in the inventive process is obtainable by
  i) impregnating a refractory support having a BET surface area in the range of 1.4 to 2.5 $m^2/g$ with a silver impregnation solution, preferably under reduced pressure; and optionally subjecting the impregnated refractory support to drying; and
  ii) subjecting the impregnated refractory support to a calcination process;
wherein steps i) and ii) are optionally.

In order to obtain a shaped catalyst body having high silver contents, steps i) and ii) can be repeated several times. In that case it is understood that the intermediate product obtained after the first (or subsequent up to the last but one) impregnation/calcination cycle comprises a part of the total amount of target Ag and/or promoter concentrations. The intermediate product is then again impregnated with the silver impregnation solution and calcined to yield the target Ag and/or promoter concentrations.

The aluminium oxide support may comprise impurities, such as sodium, potassium, iron, silica, magnesium, calcium, zirconium in an amount of 100 to 10000 ppm, based on the total weight of the support.

Any known impregnation processes known in the art can be used. Examples of suitable impregnation processes are described, e.g., in WO2013/066557 or WO2018/044992. Preferably, impregnation is conducted at a pressure of less than 250 mbar, more preferably at a pressure of less than 100 mbar.

Any calcination processes known in the art can be used. Suitable examples of calcination processes are described in U.S. Pat. Nos. 5,504,052, 5,646,087, 7,553,795, 8,378,129, 8,546,297, US2014/0187417, EP 1893331 or WO2012/140614.

The porous refractory support may be characterized by its BET surface area, total pore volume and pore size distribution, which are measured by mercury intrusion and by its water absorption. It is assumed that certain ranges of BET surface area, total pore volume and pore size distribution of the support and of the water absorption of the support are preferred in order to provide an overall improved catalyst which provides high selectivity but still has a high side crush strength.

The BET surface area of the porous refractory support is preferably in the range of 1.4 to 2.5 $m^2/g$, more preferably 1.7 to 2.3 $m^2/g$, most preferably at least 1.8 $m^2/g$, e.g., 1.9 to 2.2 $m^2/g$. The BET surface is determined according to DIN ISO 9277 herein, unless stated otherwise.

The BET surface of the shaped catalyst body is usually higher in comparison to the BET surface area of the porous refractory support. The BET surface area of the shaped catalyst body is in the range of 1.6 to 3.0 $m^2/gm$, preferably 1.8 to 2.8 $m^2/g$, more preferably 2.0 to 2.6 $m^2/g$, most preferably at least 2.3 $m^2/g$, e.g., 2.3 to 2.5 $m^2/g$.

The BET surface area of the porous refractory support can be adjusted, for example, by combining two $\alpha$-$Al_2O_3$ particles of different sizes when the refractory support is prepared (see, e.g., EP 0 902 726 B1 or WO 2011/153390 A2) or varying the calcination temperature. As pointed out in WO 2012/143559 A1, an increase in the porosity can be achieved using organic additives having a placeholder function, thereby obtaining size distributions which are directly related to the grain sizes of the raw materials used. Additional methods for preparing support materials are described in WO 2012/143559 A1 and WO 2012/143557 A1.

The water absorption of the refractory support is an indicator for the suitability of the refractory support to have an active catalyst component, such as silver, deposited thereon, for example by impregnation with a silver impregnation solution. Excessively low water absorption indicates that the generally aqueous impregnation solution does not penetrate the pores of the refractory support to a desirable degree, and impregnation may not be sufficient to obtain a desirable amount of active catalyst component in the shaped catalyst body. Excessively high water absorption, on the other hand, may cause poor mechanical strength. In general, water absorption values correlate well with the total pore volume of the support determined by mercury intrusion. However, catalyst shaped bodies with small passageways, e.g., with passageways below 1.5 mm, may display significant deviations between water absorption and the total pore volume of the support, as a part of water might be retained by passageways.

When the water absorption is more than 5% higher than the total pore volume determined by mercury intrusion, the support is impregnated based on the total pore volume determined by mercury. In some embodiments it is preferable to impregnate only a part of the support based either on water absorption or on a total pore volume determined by mercury intrusion.

The water absorption of the refractory support can, for example, be in the range of 0.35 to 0.70 mL/g (mL of water/gram of support), preferably 0.38 to 0.65 mL/g, most preferably 0.41 to 0.60 mL/g. Water absorption refers to vacuum cold water uptake measured at a vacuum of 80 mbar. Vacuum cold water uptake is determined by placing about 100 g of support ("initial support weight") in a rotating flask, covering the support with deionized water, and rotating the rotary evaporator for 5 min at about 30 rpm. Subsequently, a vacuum of 80 mbar is applied for 3 min, the water and the support are transferred into a glass funnel, and the support is kept in the funnel for about 5 min with occasional shaking in order to ensure that adhering water runs down the funnel. The support is weighed ("final support weight"). The water absorption is calculated by subtracting the initial support weight from the final support weight and then dividing this difference by the initial support weight.

The ratio of water absorption of the support (mL of water/gram of support) to BET surface area of the support ($m^2$ of support/gram of support) is in the range of 0.18 to 0.33 $mL/m^2$, preferably in the range from 0.20 to 0.30 $mL/m^2$.

The refractory support may generally be obtained by tableting of a suitable precursor material or by extrusion of a suitable precursor material through a die, and subsequent drying and calcination of the extrudate. The cross-section of the die opening is adapted according to the above embodiments.

The extrusion die may comprise a matrix and mandrels, wherein the matrix essentially determines the form, size and position of the void spaces running in the cylinder periphery and the mandrels essentially determine the form, size and position of the passageways.

The geometry of the shape of the shaped catalyst body of the invention is defined by the ideal geometry of the extrusion apparatus through which the catalyst precursor mold is extruded. Generally, the geometry of the shape of the extrudate differs slightly from the ideal geometry of the extrusion apparatus, while essentially having the geometric properties described above. Absolute sizes of the shape are in general slightly lower than the sizes of the extrudate, due to high temperatures required to form alpha alumina and shrinkage upon cooling of the extrudate. The extent of the shrinkage depends on the applied calcination temperatures. Therefore, the size of the extrusion dies should be routinely adjusted in a way to account for the extrudate shrinkage during the subsequent calcination step.

Generally, the axes of the passageways run parallel. However, the shaped catalyst bodies may be slightly bent or twisted along its z axis (height). The shape of the cross-section of the passageways may be slightly different from the perfect geometrical shapes described above. When a large amount of shaped bodies is obtained, single passageways of a small number of the shaped catalyst bodies may be closed. Usually the face sides of the shaped catalyst bodies in the xy plane are more or less uneven, rather than smooth, due to the production process. The height of the shaped bodies (length of the shaped bodies in the z direction) is usually not exactly the same for all of the shaped catalyst bodies, but rather constitutes a distribution with an average height as its arithmetic mean.

The extrudate is cut into the desired length while still wet. Preferably, the extrudate is cut at an angle essentially perpendicular to its circumferential surface. In order to reduce undesirable deviations from the ideal geometry of the extrusion apparatus, the extrudate may alternatively be cut at a slanted angle of up to 30°, such as 10° or 20°, with regard to the angle perpendicular to the circumferential surface of the extrudate.

Aberrations from the ideal geometry as incurred in the extrusion process and/or the further processing of the extrudate, e.g. a cutting step, may generally also be present in the shaped catalyst body of the invention without essentially lessening the favorable effects of its geometry. The skilled person understands that perfect geometrical forms are fundamentally unobtainable due to the imprecision which is inherent to all production processes to some degree.

As the inventive catalyst is obtained by impregnating a refractory support, the geometry of the refractory support largely dictates the geometry of the catalyst bodies. Nevertheless, the process of impregnating can result in minor deviations of the shape of the final catalyst from that of the refractory support. For example, the exposed edges and surfaces of the carrier may undergo a degree of abrasion upon mechanical strain, such as tumbling, which an impregnation process typically comprises. Furthermore, although the major amount of silver is deposited in the pores and the inner surfaces of the carrier, minor amounts of silver are deposited on the outer surfaces of the carrier, in particular in concave areas of the circumference and the passageways. Typically, however, no linear geometric dimension of the catalyst and the refractory support deviates by more than 15% or more than 10%, such as more than 5%, relative to the linear geometric dimension of the refractory support.

Any silver impregnation solution suitable for impregnating a refractory support known in the art can be used. Silver impregnation solutions typically contain silver oxalate, or a combination of silver oxide and oxalic acid, together with ethylenediamine. Suitable impregnation solutions are described in EP 0 716 884 A2, EP 1 115 486 A1, EP 1 613 428 A1, U.S. Pat. No. 4,731,350, WO 2004/094055 A2, WO 2009/029419 A1, WO 2015/095508 A1, U.S. Pat. Nos. 4,356,312, 5,187,140, 4,908,343, 5,504,053 and WO 2014/105770 A1.

Any impregnation processes known in the art can be used. A suitable example of an impregnation process is described in WO 2013/066557.

It is possible to establish the desired composition of the catalyst with relative amounts of all metals as desired in only one impregnation. Alternatively, impregnation step i) may comprise multiple alternating impregnation and drying steps. The impregnation solution in a first impregnation step comprises for example silver and promotor, e.g. rhenium and/or cesium. Additional promotors, such as tungsten, lithium, and/or sulfur can, for example, be comprised by a silver impregnation solution used in a second or later impregnation step.

The impregnated refractory support is subjected to a calcination process ii). Any calcination processes known in the art can be used. Suitable examples of calcination processes are described in U.S. Pat. Nos. 5,504,052, 5,646,087, 7,553,795, 8,378,129, 8,546,297, US 2014/0187417, EP 1893331 or WO 2012/140614.

The calcination process is usually carried out in a furnace. The type of furnace is not especially limited. For example, stationary circulating air furnaces, revolving cylindrical furnaces or conveyor furnaces may be used. The duration of the calcination process is generally in the range of 5 min to 20 h, preferably 5 min to 30 min. The temperature of the calcination process is generally in the range of 200 to 800° C.

It may be favorable to sort the shaped catalyst body or its precursors according to size and use only a fraction of suitable size. This sorting may be performed after the calcination or at another suitable point of time during the production process. The sorting may be achieved by using suitable sieves. Shaped bodies which are larger or smaller than the desired dimensions may be recycled as return material to suitable points of the process. It may be preferable to subject the return material to further processing steps, such as a grinding step, prior to recycling.

The process for producing ethylene oxide by gas-phase oxidation of ethylene, comprises reacting ethylene and oxygen in the presence of a shaped catalyst body as discussed above.

It has been found that the physical characteristics of the catalyst, especially the BET surface area, the pore size distribution, and shape of the catalyst body, have a significant positive impact on the catalyst selectivity. This effect is especially distinguished when the catalyst is operated at very high work rates, i.e., high levels of olefin oxide production.

The process according to the invention is carried out under conditions conducive to obtain a reaction mixture containing at least 2.7 vol.-% of ethylene oxide. In other words, the ethylene oxide outlet concentration (ethylene oxide concentration at the reactor outlet) is at least 2.7 vol.-%. The ethylene oxide outlet concentration is preferably in the range of 2.8 to 4.0 vol.-%, more preferably in the range of 2.9 to 3.5 vol.-%.

The GHSV (gas hourly space velocity) is, depending on the type of reactor chosen, for example on the size/cross-sectional area of the reactor, the shape and size of the catalyst, preferably in the range from 800 to 10,000/h, preferably in the range from 2,000 to 8,000/h, more preferably in the range from 2,500 to 6,000/h, most preferably 4,500 to 5,500/h where the values indicated are based on the volume of the catalyst.

According to a further embodiment, the present invention is also directed to a process for preparing ethylene oxide (EO) by gas-phase oxidation of ethylene by means of oxygen as disclosed above, wherein the EO-space-time-yield measured is greater than 250 $kg_{EO}/(m^3_{cat}h)$, preferably to an EO-space-time-yield of greater than 280 $kg_{EO}/(m^3_{cat}h)$, more preferably to an EO-space-time-yield of greater than 300 $kg_{EO}/(m^3_{cat}h)$. Preferably the EO-space-time-yield measured is less than 500 $kg_{EO}/(m^3_{cat}h)$, more preferably the EO-space-time-yield is less than 350 $kg_{EO}/(m^3_{cat}h)$.

The epoxidation can be carried out by processes known to those skilled in the art. It is possible to use reactors which can be used in the ethylene oxide production processes of the prior art; for example externally cooled shell-and-tube reactors (cf. Ullmann's Encyclopedia of Industrial Chemistry, 5th edition, vol. A-10, pp. 117-135, 123-125, VCH-Verlagsgesellschaft, Weinheim 1987) or reactors having a loose catalyst bed and cooling tubes, for example the reactors described in DE-A 3414717, EP 0082609 and EP-A 0339748.

The epoxidation is preferably carried out in at least one tube reactor, preferably in a shell-and-tube reactor. On a commercial scale, ethylene epoxidation is preferably carried out in a multi-tube reactor that contains several thousand tubes. The catalyst is filled into the tubes, which are placed in a shell that is filled with a coolant. In commercial applications, the internal tube diameter is typically in the range of 20 to 40 mm (see, e.g., U.S. Pat. No. 4,921,681) or more than 40 mm (see, e.g., WO2006/102189).

To prepare ethylene oxide from ethylene and oxygen, it is possible to carry out the reaction under conventional reaction conditions as described, for example, in DE-A 2521906, EP-A 0 014 457, DE-A 2300512, EP-A 0 172 565, DE-A 2454972, EP-A 0 357 293, EP-A 0 266 015, EP-A 0 085 237, EP-A 0 082 609 and EP-A 0 339 748. Inert gases such as nitrogen or gases which are inert under the reaction conditions, e.g. steam, methane, and also optionally reaction moderators, for example halogenated hydrocarbons such as ethyl chloride, vinyl chloride or 1,2-dichloroethane can additionally be mixed into the reaction gas comprising ethylene and molecular oxygen.

The oxygen content of the reaction gas is advantageously in a range in which no explosive gas mixtures are present. A suitable composition of the reaction gas for preparing ethylene oxide can, for example, comprise an amount of ethylene in the range from 10 to 80% by volume, preferably from 20 to 60% by volume, more preferably from 25 to 50% by volume and particularly preferably in the range from 25 to 40% by volume, based on the total volume of the reaction gas. The oxygen content of the reaction gas is advantageously in the range of not more than 10% by volume, preferably not more than 9% by volume, more preferably not more than 8% by volume and very particularly preferably not more than 7.5% by volume, based on the total volume of the reaction gas.

The reaction gas preferably comprises a chlorine-comprising reaction moderator such as ethyl chloride, vinyl chloride or 1,2-dichloroethane in an amount of from 0 to 15 ppm by weight, preferably in an amount of from 0.1 to 8 ppm by weight, based on the total weight of the reaction gas. The remainder of the reaction gas generally comprises hydrocarbons such as methane and also inert gases such as nitrogen. In addition, other materials such as steam, carbon dioxide or noble gases can also be comprised in the reaction gas.

The concentration of carbon dioxide in the feed (i.e. the gas mixture fed to the reactor) typically depends on the catalyst selectivity and the efficiency of the carbon dioxide removal equipment. Carbon dioxide concentration in the feed is preferably at most 3 vol-%, more preferably less than 2 vol-%, most preferably less than 1 vol-%, relative to the total volume of the feed. An example of carbon dioxide removal equipment is provided in U.S. Pat. No. 6,452,027.

The above-described constituents of the reaction mixture may optionally each have small amounts of impurities. Ethylene can, for example, be used in any degree of purity suitable for the gas-phase oxidation according to the invention. Suitable degrees of purity include, but are not limited to, "polymer-grade" ethylene, which typically has a purity of at least 99%, and "chemical-grade" ethylene which typically has a purity of less than 95%. The impurities typically comprise, in particular, ethane, propane and/or propene.

The reaction or oxidation of ethylene to ethylene oxide is usually carried out at elevated catalyst temperatures. Preference is given to catalyst temperatures in the range of 150 to 350° C., more preferably 180 to 300° C., particularly preferably 190 to 280° C. and especially preferably 200 to 280° C. The ethylene oxide outlet concentration adjustments are achieved by increasing the catalyst temperature and thereby increasing the ethylene and oxygen conversion. Catalyst temperature can be determined by thermocouples located inside the catalyst bed. As used herein, the catalyst temperature or the temperature of the catalyst bed is deemed to be the weight average temperature of the catalyst particles.

The reaction according to the invention (oxidation) is preferably carried out at pressures in the range of 5 to 30 bar. All pressures herein are absolute pressures, unless noted otherwise. The oxidation is more preferably carried out at a pressure in the range of 5 to 25 bar, such as 10 bar to 20 bar and in particular 14 bar to 20 bar. The present invention therefore also provides a process as described above in which the oxidation is carried out at a pressure in the range of 14 bar to 20 bar.

The preparation of ethylene oxide from ethylene and oxygen can advantageously be carried out in a recycle process. After each pass, the newly formed ethylene oxide and the by-products formed in the reaction are removed from the product gas stream. The remaining gas stream is supplemented with the required amounts of ethylene, oxygen and reaction moderators and reintroduced into the reactor. The separation of the ethylene oxide from the product gas stream and its work-up can be carried out by customary methods of the prior art (cf. Ullmann's Encyclopedia of Industrial Chemistry, 5th edition, vol. A-10, pp. 117-135, 123-125, VCH-Verlagsgesellschaft, Weinheim 1987).

The invention will be described in more detail by the accompanying drawings and the subsequent examples.

FIGS. 2a, 2b and 2c show a schematic cross-section of a shaped catalyst body according to FIG. 1a.

FIG. 3 shows a schematic side-view of a shaped catalyst body according to FIG. 1a.

Figure 1A:
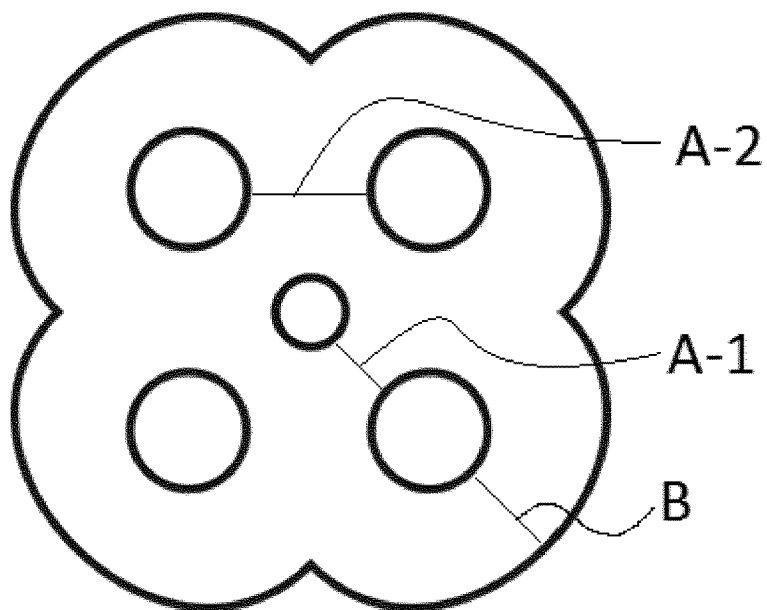
FIGS. 1a and 1b show schematic exemplary cross-sections of shaped catalyst bodies of the invention.
Figure 1B:
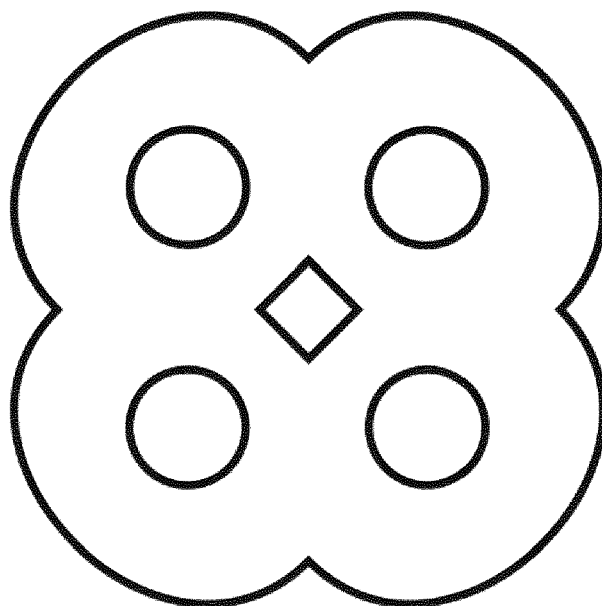

With regard to FIGS. 1a and 1b, the shaped catalyst bodies have four outer passageways arranged equidistantly around a central passageway and have a 4-fold rotational symmetry. According to FIG. 1a, the four outer passageways and the central passageway have a circular cross-section. According to FIG. 1b, the four outer passageways have a circular cross-section and the central passageway has a cross-section in the shape of a square.

For illustrative purposes, FIG. 1a shows the distance A-1 between a central passageway and a neighboring outer passageway, and the distance A-2 between two neighboring outer passageways. Further, FIG. 1a shows the distance B between a passageway and the circumferential surface. Distances A-2 and B are essentially equal.

Figure 2A:
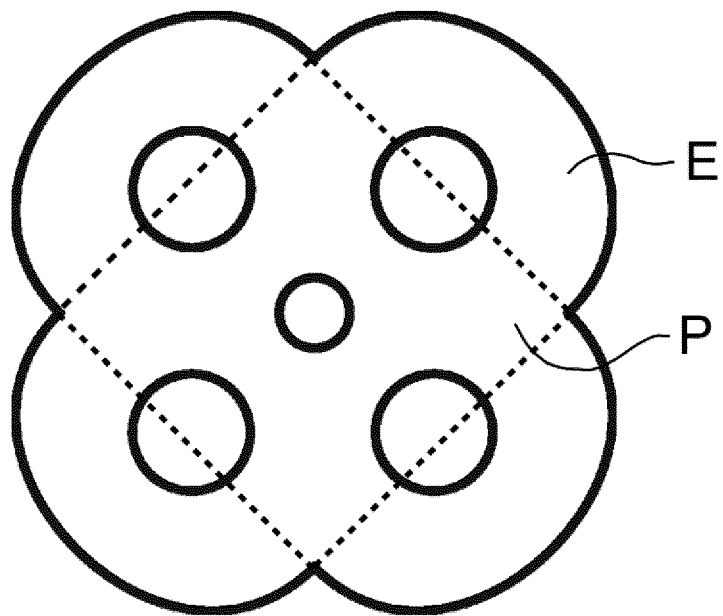
Figure 2B:
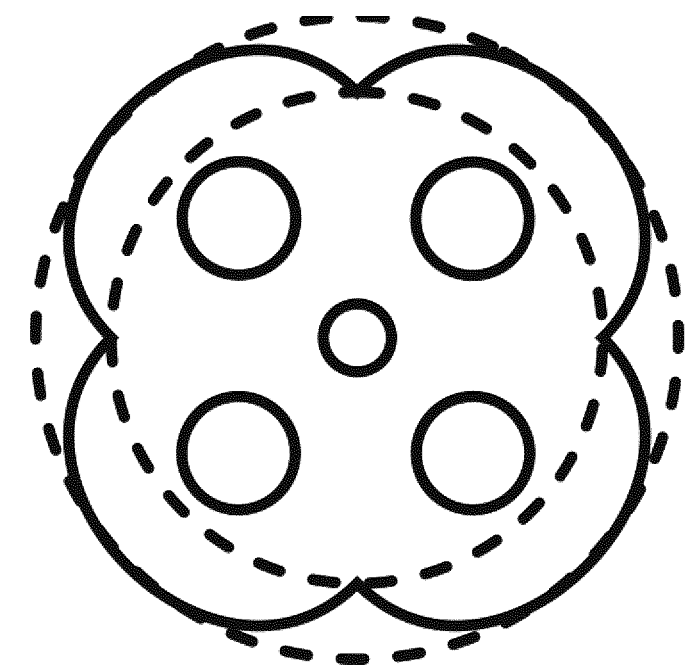

FIGS. 2a and 2b show a schematic cross-section of a shaped catalyst body according to FIG. 1a. The cross-section is derived from a circular-cylinder structure with a plurality of void spaces. The cross-section has the shape of a substantially equilateral, equiangular polygon with elliptical segments attached to each side.

In FIG. 2a, the sides of the substantially equilateral, equiangular polygon P are indicated by dashed lines. The elliptical segments E traverse the side they are attached to and meet at the corners of the polygon P.

In FIG. 2b, the circumscribed circle and the inscribed circle are indicated by dashed lines.

Figure 2C:
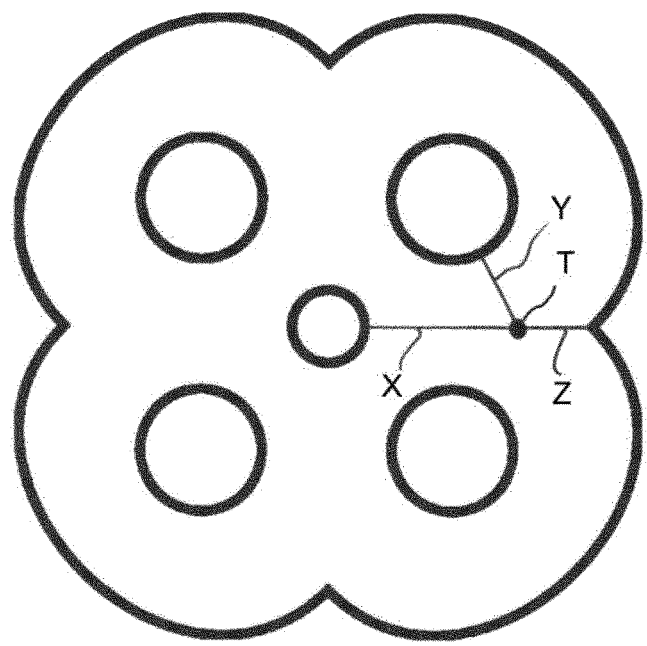
Figure 2D:
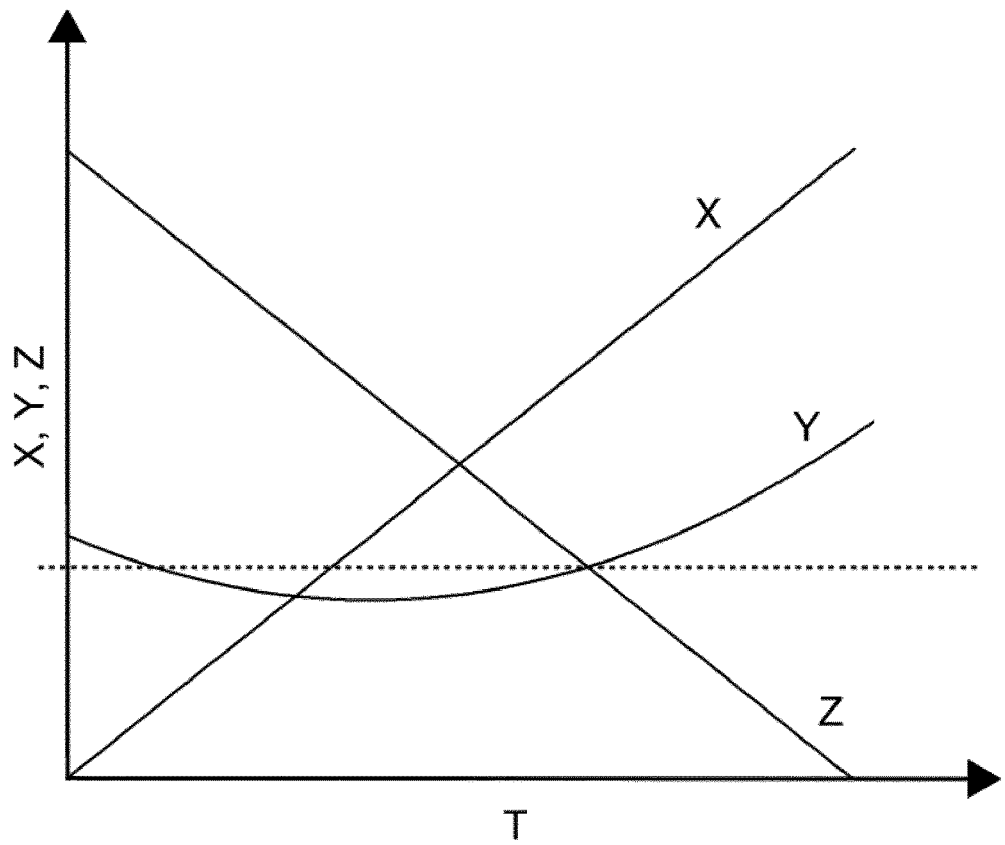
FIG. 2d shows a graphical representation of the distances within the cross-section of a shaped catalyst body according to a catalyst of the invention relevant for determining the longest direct diffusion pathway.

Determination of the longest direct diffusion pathway is illustrated in FIGS. 2c and 2d for the catalyst 2.5: When the point T travels along a line from the central passageway to the circumferential indentation, distance Z to the circumferential surface decreases, whereas distance X to the central passageway increases. Distance Y to the outer passageway undergoes a minimum. The intersection of the graphs for Y and Z corresponds to the longest direct pathway d. In FIG. 2d, the dotted line indicates the point where Y=Z, and thus the longest diffusion pathway d.

Figure 3:
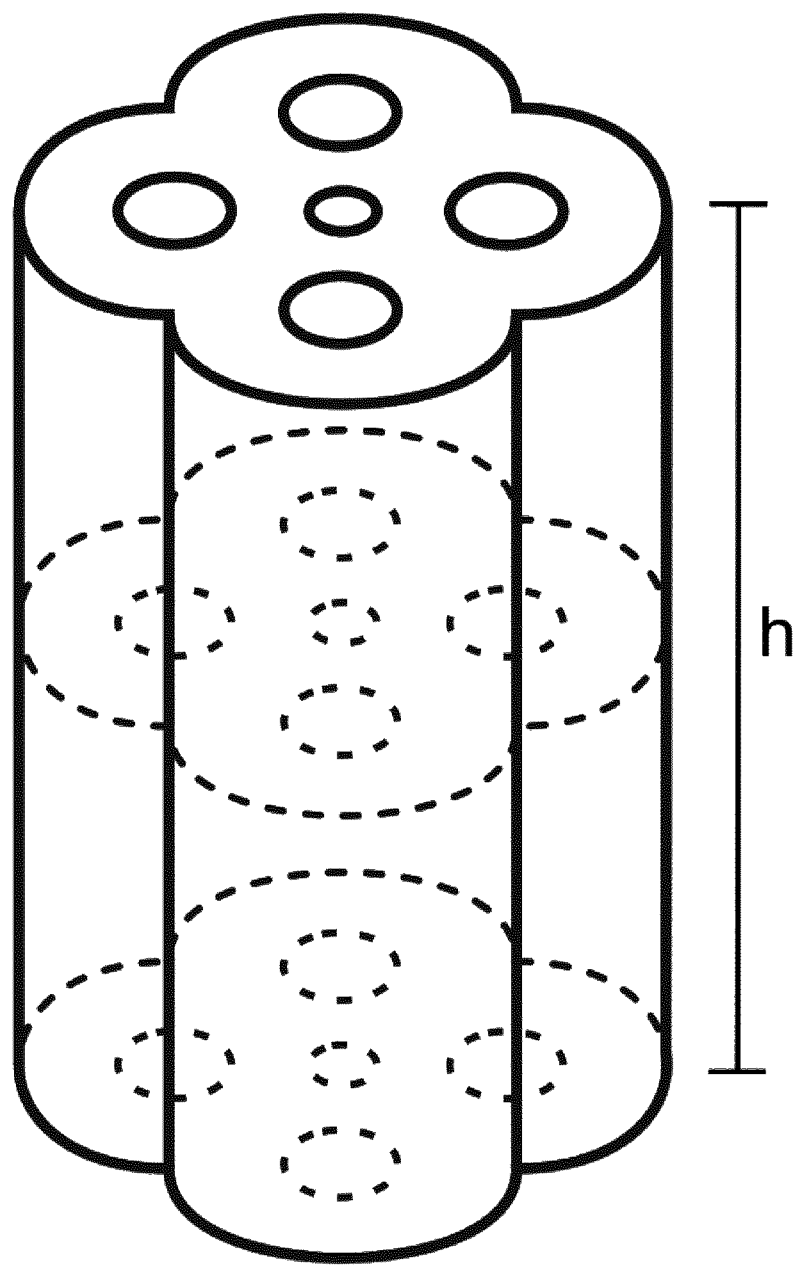

FIG. 3 shows a schematic side-view of a shaped catalyst body according to FIG. 1a, wherein cross-sections are shown as dashed lines. The height h of the shaped catalyst body is indicated.

Figure 4:
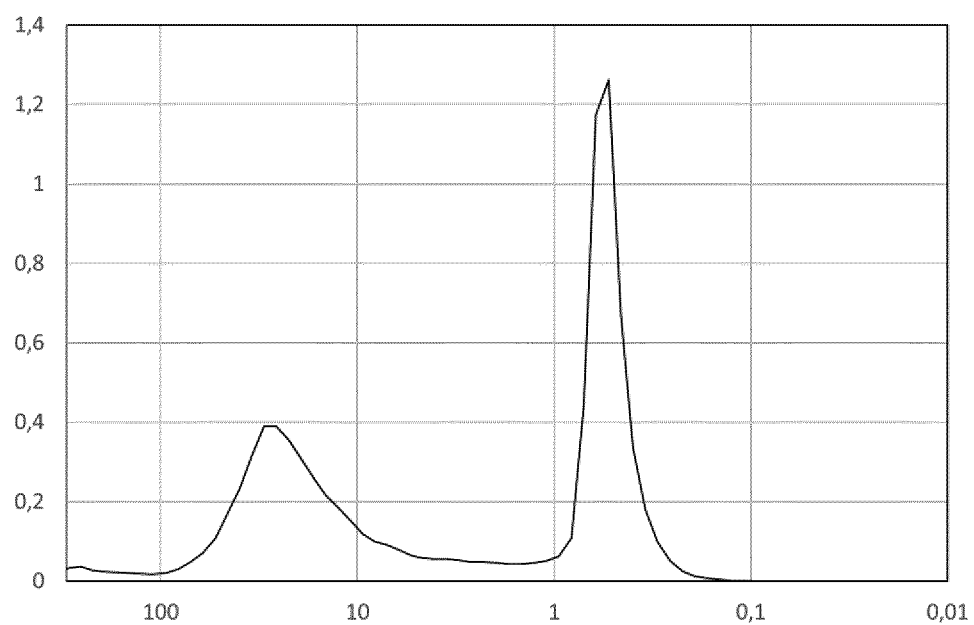
FIG. 4 shows the pore size distribution of a preferred refractory support.

FIG. 4 shows the pore size distribution of the refractory support D, as determined by mercury porosimetry. On the x-axis, the pore size diameter [μm] is plotted. On the y-axis, the log differential intrusion [mL/g] is plotted.

Figure 5:
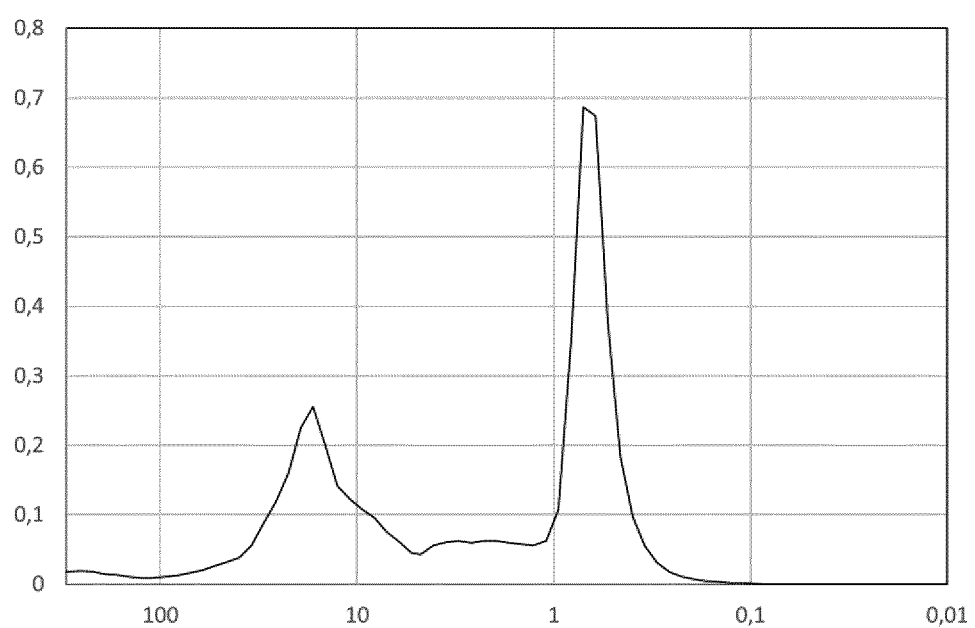
FIG. 5 and FIG. 6 show the pore size distribution of preferred shaped catalyst bodies according to the invention.

FIG. 5 shows the pore size distribution of the catalyst 2.4, as determined by mercury porosimetry. On the x-axis, the pore size diameter [μm] is plotted. On the y-axis, the log differential intrusion [mL/g] is plotted in.

Figure 6:
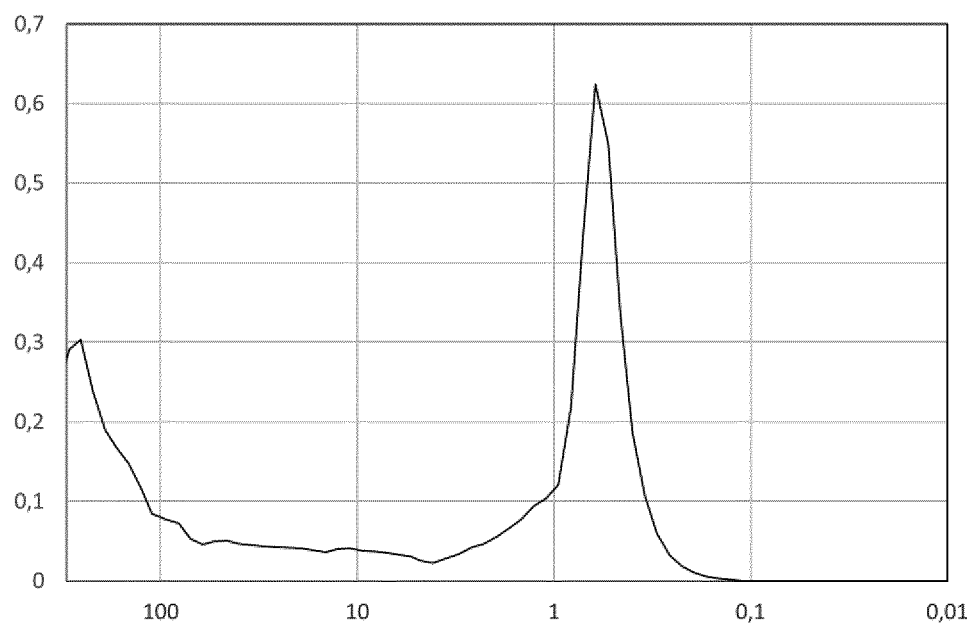

FIG. 6 shows the pore size distribution of the catalyst 2.5, as determined by mercury porosimetry. On the x-axis, the pore size diameter [μm] is plotted. On the y-axis, the log differential intrusion [mL/g] is plotted in.

Figure 7:
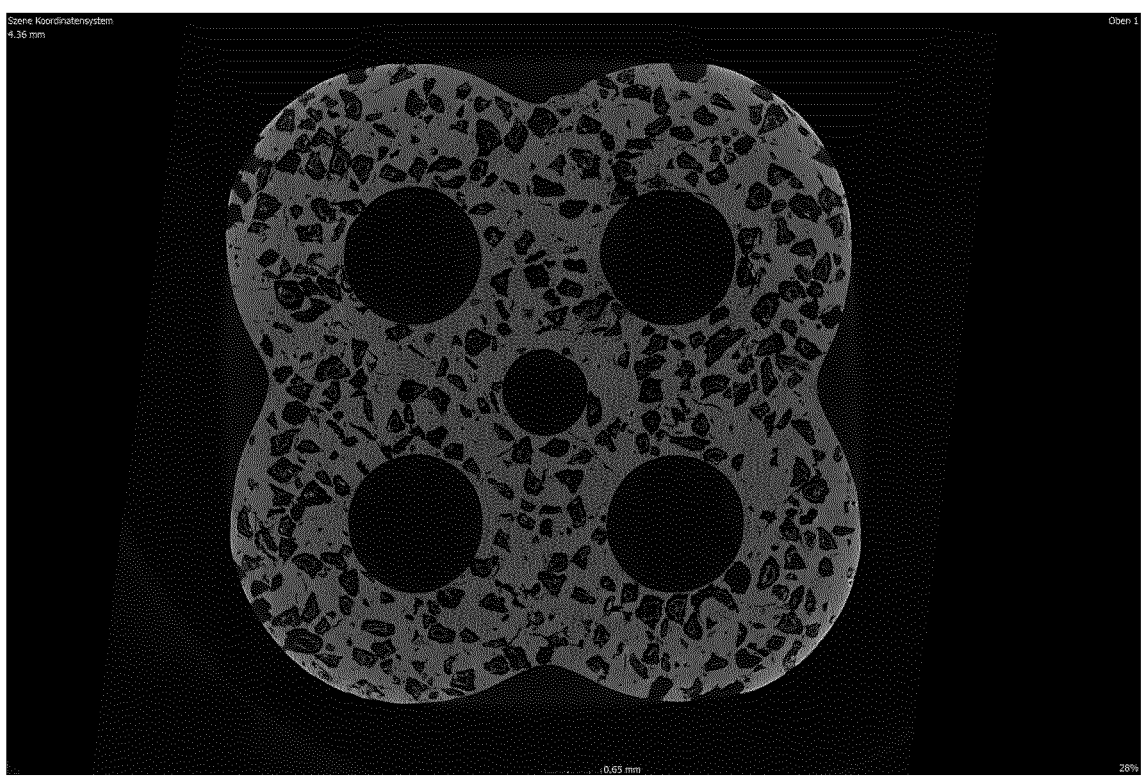
FIG. 7 shows the cross-section of a support useful for providing a shaped catalyst body of the invention.

FIG. 7 shows a scan of the cross-section of support Q obtained by Computed Tomography.

EXAMPLES

Methods and Materials

Methods

Method 1—Experimental Measurement of the Pressure Drop

The pressure drop coefficient ξ is proportional to the pressure drop and is defined as $$\xi = \frac{\Delta p}{H} \cdot d_k \cdot \frac{2}{\rho \cdot w^2}$$

with the pressure drop Δp in Pascal, the height of the packing H in meters, the constant reference length $d_K$ of 0.01 meters, the average gas density ρ in kg/m³ and the average superficial gas velocity w in m/s.

The pressure drop coefficient ξ can be described using the following equalization function:

$$\xi = a + \frac{b}{Re_{dk10}}$$

where the Reynolds number $Re_{dk10}$ is defined as $$Re_{dk10} = \frac{w \cdot d_k \cdot \rho}{\eta}$$

with the dynamic viscosity of the gas η in Pascal·seconds. The parameters a and b can be obtained by linear regression from experimental values. A suitable Reynolds number in an ethylene oxide process is between 5,000 and 6,000, for example 5,500.

Method 2—Simulation of the Pressure Drop

The correlation between pressure drop and catalyst shape was calculated via numerical flow simulation, which completely resolves the flow in the spaces between the catalyst bed. The procedure consists of three consecutive steps. First, the geometry of the bed is created. For this purpose, a CAD (Computer Aided Design) model of a single shaped catalyst body is created with any CAD program. This determines the shape of the catalyst (e.g. cylinder, ring, multilobe, etc.). A tube with an internal diameter typical of a technical reactor (39.5 mm) is used as the outer container for the bulk material. Both the digital container geometry and the digital catalyst geometry are fed into a simulation program which makes it possible to calculate the arrangement of the shaped catalyst bodies as they are filled into the container, using Newton's equations of motion. Pressure drop calculations were performed with air at ambient temperature and different gas space velocities (GHSV, gas hourly space velocity). Values from the scientific literature for air at a constant operating pressure of 1 bar and temperature of 20° C. were used for the thermodynamic and transport properties of the gas. The reference length used to calculate the Reynolds number is defined as 0.01 meters.

Method 3—Mercury Porosimetry

Mercury porosimetry was performed using a Micrometrics AutoPore IV 9500 mercury porosimeter (140 degrees contact angle, 485 dynes/cm Hg surface tension, 60000 psia max head pressure). The Hg porosity is determined in accordance with DIN 66133.

Method 4—BET Surface Area

The BET surface area was determined in accordance with DIN ISO 9277.

Method 5—Water Absorption

Water absorption refers to vacuum cold water uptake. Vacuum cold water uptake is determined by placing about 100 g of support ("initial support weight") in a rotating flask, covering the support with deionized water, and rotating the rotary evaporator for 5 min at about 30 rpm. Subsequently, a vacuum of 80 mbar is applied for 3 min, the water and the support are transferred into a glass funnel, and the support is kept in the funnel for about 5 min with occasional shaking in order to ensure that adhering water runs down the funnel.

The support is weighed ("final support weight"). The water absorption is calculated by subtracting the initial support weight from the final support weight and then dividing this difference by the initial support weight.

Method 6—Side Crush Strength

The side crush strength was determined using an apparatus of the "Z 2.5/T 919" type supplied by Zwick Röll (Ulm), stamp size: 12.7 mm×12.7 mm. Based on measurements of 25 randomly selected shaped bodies, average values were calculated. The measurements of tetralobes were performed along two directions—along the side and along the diagonal. In the measurement along the diagonal, the force is exerted along an axis running through a first outer passageway, the central passageway and a second outer passageway opposite to the first outer passageway. In the measurement along the side, the force is exerted along two axes each running through a two outer passageways.

Method 7—Packing Tube Density

Packing tube density was determined by filling catalyst shaped bodies in a glass tube with an inner diameter of 39 mm to a marker marking an inner tube volume of 1 L.

Method 8—Geometric Measurements

Geometric dimensions were measured using a caliper with the accuracy of 0.01 mm. Reported are average values of 25 randomly selected shaped bodies.

Alternatively, geometric dimensions were measured using 3-dimensional Computed Tomography (CT) X-ray Scanning. CT data were collected using Phoenix Nanotom M (General Electric), scan time=1 h, 150 kV/80 ρA, resolution=21.67 μm/Voxel size. This method is a preferable way for geometric measurements of complex shapes within the scope of claims of the current invention. Results are provided as average values of 28 randomly selected shaped bodies.

Method 9—Simulation of Geometric Surface and Geometric Volume

A CAD (Computer Aided Design) model of a single shaped catalyst body is created with any CAD program to calculate the geometric surface and geometric volume.

Method 10—Analysis of Silver Content

Shaped catalyst bodies were crushed and pulverized so as to obtain homogenized samples. 300 to 700 mg of pulverized catalyst bodies were weighed into a titrator (888 Titrando, Metrohm). The sample was brought into contact with 10 mL of a mixture of 65% $HNO_3$:$H_2O$ (1:1) at boiling temperature. The obtained mixture was diluted with 150 mL of $H_2O$ and titrated with a 0.1 M solution of ammonium thiocyanate, using a silver electrode.

Refractory Supports

The refractory supports were alumina supports and comprised Si, Ca, Mg, Na, K and Fe as chemical impurities. The properties of the refractory supports are indicated in Table 1 below. The supports were obtained from EXACER s.r.l. (Via Puglia 2/4, 41049 Sassuolo (MO), Italy), under the following lot numbers:

| A | COM 84/13 |
|---|---|
| B | COM 63/17 86/17S |
| C | Bimal 889 |
| D | Q888 |
| E | Q901 |
| F | Q902 |
| G | Q903 |
| H | Q904 |
| I | Q905 |
| K | Q908 |
| L | Q907 |
| M | Q909C |
| N | Q909L |
| O | Q910 |
| P | Q920 |
| Q | COM 48/18 |

Support A has $Si_{Al2O3}$=400 ppm, $Ca_{Al2O3}$=200 ppm, $Mg_{Al2O3}$=100 ppm, $Na_{Al2O3}$=80 ppm, $K_{Al2O3}$=60 ppm, $Fe_{Al2O3}$=200 ppm. The supports B to P have $Si_{Al2O3}$=500 ppm, $Ca_{Al2O3}$=400 ppm, $Mg_{Al2O3}$=200 ppm, $Na_{Al2O3}$=100 ppm, $K_{Al2O3}$=185 ppm, $Fe_{Al2O3}$=100 ppm. Support Q has $Si_{Al2O3}$=450 ppm, $Ca_{Al2O3}$=350 ppm, $Mg_{Al2O3}$=130 ppm, $Na_{Al2O3}$=100 ppm, $K_{Al2O3}$=150 ppm, $Fe_{Al2O3}$=150 ppm.

Support A has a bimodal pore size distribution with the first log differential pore volume distribution peak at 1.2 μm and the second log differential pore volume distribution peak at 49 μm. The supports B to Q have a bimodal pore size distribution with smaller pores with the first log differential pore volume distribution peak in the range of 0.4 to 0.6 μm and the second log differential pore volume distribution peak in the range of 17 to 30 μm.

The cross-section of all passageways of the refractory supports had a circular shape, with the exception of the central passageways of support H and support L. The cross-sections of the central passageways of support H and support L were pincushion-shaped.

TABLE 1

| | A[1] | B[1] | C[1] | D | E | F | G | H | I | K | L | M | N | O | P | Q |
|---|---|---|---|---|---|---|---|---|---|---|---|---|---|---|---|---|
| Shape | ring | | | | | | | | | tetralobe | | | | | | |
| Geometry / Passageways | | | | | | | | | | | | | | | | |
| diameter of circumscribed circle $d_{cc}$ [mm] | 8.0 | 9.7 | 8.4 | 8.5 | 8.5 | 8.5 | 8.5 | 8.5 | 8.5 | 9.1 | 9.0 | 8.5 | 8.5 | 7.3 | 8.85 | 8.72 |
| diameter of inscribed circle $d_{ic}$ [mm] | 8.0 | 9.7 | 8.4 | 6.5 | 6.5 | 6.5 | 6.5 | 6.5 | 6.5 | 6.5 | 6.5 | 6.5 | 6.5 | 5.7 | 5.9 | 6.46 |
| quotient $d_{ic}/d_{cc}$ | 1 | 1 | 1 | 0.76 | 0.76 | 0.76 | 0.76 | 0.76 | 0.76 | 0.71 | 0.72 | 0.76 | 0.76 | 0.78 | 0.67 | 0.74 |
| height h [mm] | 7.9 | 9.7 | 8.5 | 8.5 | 8.5 | 8.5 | 8.4 | 8.6 | 8.1 | 8.0 | 8.3 | 7.6 | 9.8 | 6.7 | 9.0 | 8.5 |
| quotient $d_{cc}/h$ | 1.01 | 1.00 | 0.99 | 1.00 | 1.00 | 1.00 | 1.01 | 0.99 | 1.05 | 1.14 | 1.08 | 1.12 | 0.87 | 1.09 | 0.98 | 1.03 |
| diameter of four outer passageways [mm] | — | — | — | 1.3 | 1.4 | 1.4 | 1.5 | 1.4 | 1.5 | 1.5 | 1.5 | 1.5 | 1.5 | 1.2 | 1.55 | 1.6 |
| diameter of central passageway [mm] | 2.6 | 2.9 | 2.8 | 0.9 | 1.0 | 1.3 | 0.8 | 1.4[2] | 0.9 | 1.1 | 1.3[2] | 0.9 | 0.9 | 0.8 | 1.3 | 1.0 |
| distance A [mm] | — | — | — | 1.0 | 0.9 | 0.75 | 0.95 | 0.8 | 0.9 | 1.05 | 0.95 | 0.9 | 0.9 | 0.75 | 0.9 | 0.9 |
| distance B [mm] | 2.7 | 3.4 | 2.8 | 1.5 | 1.45 | 1.45 | 1.4 | 1.45 | 1.4 | 1.45 | 1.5 | 1.4 | 1.4 | 1.3 | 1.3 | 1.4 |
| distance between outer passageways [mm] | — | — | — | 1.64 | 1.60 | 1.55 | 1.51 | 1.55 | 1.52 | 1.79 | 1.79 | 1.52 | 1.52 | 1.33 | 1.77 | 1.47 |
| distance between central passageway and outer passageways [mm] | — | — | — | 1.0 | 0.9 | 0.75 | 0.95 | 0.8 | 0.9 | 1.05 | 0.95 | 0.9 | 0.9 | 0.75 | 0.9 | 0.9 |
| thickness (2d) | 2.7 | 3.4 | 2.8 | n.d. | n.d. | n.d. | n.d. | n.d. | n.d. | n.d. | n.d. | n.d. | n.d. | n.d. | 1.82 | 1.88 |
| ratio of total cross-sectional area of passageways to cross-sectional area of shaped catalyst body | 0.11 | 0.09 | 0.11 | n.d. | n.d. | n.d. | n.d. | n.d. | n.d. | n.d. | n.d. | n.d. | n.d. | n.d. | 0.19 | n.d. |
| geometric surface area $SA_{geo}$ [mm²] | 353 | 518 | 397 | 459 | 471 | 478 | 470 | n.d. | 459 | n.d. | n.d. | 435 | 538 | n.d. | 543 | n.d. |
| geometric volume $V_{geo}$ [mm³] | 355 | 652 | 418 | 358 | 349 | 345 | 340 | n.d. | 327 | n.d. | n.d. | 307 | 395 | n.d. | 357 | n.d. |
| quotient $SA_{geo}/V_{geo}$ [mm⁻¹] | 0.99 | 0.79 | 0.95 | 1.28 | 1.35 | 1.39 | 1.38 | n.d. | 1.40 | n.d. | n.d. | 1.42 | 1.36 | n.d. | 1.52 | n.d. |
| Physical Properties | | | | | | | | | | | | | | | | |
| BET surface area [m²/g] | 0.71 | 2.02 | 1.95 | 2.03 | 2.06 | 2.04 | 1.98 | 1.98 | 1.99 | 2.07 | 2.08 | 2.06 | 2.06 | 2.08 | 2.09 | 1.95 |
| water uptake [mL/g] | 0.46 | 0.55 | 0.55 | 0.59 | 0.58 | 0.58 | n.d.[6] | n.d. | n.d. | n.d. | n.d. | 0.58 | 0.57 | 0.62 | 0.56 | 0.57 |
| total Hg pore volume [mL/g] | 0.45 | 0.59 | 0.52 | 0.56 | 0.53 | 0.52 | 0.55 | 0.54 | 0.53 | 0.53 | 0.58 | 0.51 | 0.51 | 0.54 | 0.54 | 0.53 |
| 1st log diff. peak [μm][4] | 1.5 | 0.6 | 0.4 | 0.5 | 0.4 | 0.4 | 0.4 | 0.4 | 0.4 | 0.4 | 0.4 | 0.4 | 0.4 | 0.4 | 0.4 | 0.4 |
| 2nd log diff. | 46 | 17 | 21 | 26-30 | 22 | 22 | 27 | 22 | 24 | 20 | 24 | 23 | 23 | 25 | 25 | 30 |

TABLE 1-continued

| | A[1] | B[1] | C[1] | D | E | F | G | H | I | K | L | M | N | O | P | Q |
|---|---|---|---|---|---|---|---|---|---|---|---|---|---|---|---|---|
| Shape | ring | | | | Passageways | | | | | tetralobe | | | | | | |
| peak [μm][4] | 1 | 1 | 1 | 5 | 5 | 5 | 5 | 5 | 5 | 5 | 5 | 5 | 5 | 5 | 5 | 5 |
| Percentage of pores with a diameter of 0.1 to 3 μm [%][5] | 46 | 64 | n.d. | 54 | n.d. | n.d. | n.d. | n.d. | n.d. | n.d. | n.d. | n.d. | n.d. | n.d. | 56 | 55 |
| carrier density [g/L][3] | 700 | 588 | 621 | 579 | 564 | 555 | 568 | 558 | 571 | 539 | 520 | 559 | 561 | 597 | 540 | 577 |
| side crush strength [N] along diagonal | 98 | 74 | 50 | 70 | 51 | 52 | 55 | 40 | 54 | 58 | 57 | 42 | 56 | 46 | 60 | 76 |
| side crush strength [N] along side | n.d. | n.d. | n.d. | 92 | 74 | 62 | 73 | 41 | 77 | 75 | 60 | 77 | 99 | 68 | 93 | 111 |
| Pressure Drop Data[3] | | | | | | | | | | | | | | | | |
| a | n.d. | n.d. | n.d. | 22.3 | 19.8 | 22.3 | 21.1 | 20.7 | 20.0 | 17.3 | 18.6 | 21.7 | 21.6 | 33.0 | 18.5 | 19.7 |
| b | n.d. | n.d. | n.d. | 3,980 | 5,169 | 2,809 | 2,128 | 2,718 | 1,994 | 2,078 | 1,640 | 3,726 | 2,332 | 4,062 | 1,373 | 2,354 |
| Relative pressure drop coefficient at Re = 5,500 [%][7] | n.d. | n.d. | n.d. | 100 | 90 | 99 | 93 | 92 | 88 | 77 | 82 | 97 | 96 | 146 | 82 | 87 |

[1] Reference Example
[2] pincushion-shaped cross-section; diameter = longest possible distance between two points on the circumference of the passageway's cross-section
[3] measured in a tube with a diameter of 39 mm
[4] log diff. peak = log differential pore volume distribution peak
[5] based on the total Hg pore volume
[6] n.d. = not determined
[7] relative to support D Example 1—Simulation of the Pressure Drop The pressure drop induced by varying catalyst body geometries was additionally calculated by the above-described method 2. It should be appreciated that the calculation is based on the assumption that all catalyst bodies have exactly the same height (whereas the height of industrially produced shaped catalyst bodies is subject to a height distribution around an average height). The following geometries were examined:
- 1-1: geometry corresponds to an ideal cylinder with a height of 8.0 mm, a diameter of 8.0 mm and an inner diameter of 2.6 mm
- 1-2: geometry corresponds to a cylinder with a height of 8.0 mm, a diameter of 8.0 mm, seven passageways with a cylindrical cross-section and a diameter of 1.22 mm (one passageway being central and the others being regularly spaced on a circle with a diameter of 4.39 mm, concentric to the circumference of the cylinder); according to examples 1 to 8 of U.S. Pat. No. 4,837,194
- 1-3: geometry corresponds to support I, except for the height, which was 7.5 mm
- 1-4: geometry corresponds to support M, except for the height, which was 8.5 mm
- 1-5: geometry corresponds to support N, except for the height, which was 9.5 mm
- 1-6: geometry corresponds to support P
- 1-7: geometry essentially corresponds to support Q
- 1-8: geometry corresponds to a tetralobe with a height of 14.05 mm, an outer diameter of 8.5 mm, one central passageway with a cylindrical cross-section and an inner diameter of 1.24 mm, and rounded edges calculated on the basis of FIGS. 2 and 3 of US 2015/0045565

TABLE 2

|  | 1-1 * | 1-2 * | 1-3 | 1-4 | 1-5 | 1-6 | 1-7 | 1-8 * |
|---|---|---|---|---|---|---|---|---|
|  | | | | shape | | | | |
|  | hollow cylinder | 7-hole cylinder | tetralobe | tetralobe | tetralobe | tetralobe | tetralobe | tetralobe |
| $SA_{geo}$ [mm$^2$] | 355 | 498 | 431 | 477 | 524 | 543 | 528 | 504 |
| $V_{geo}$ [mm$^3$] | 359 | 339 | 303 | 343 | 383 | 357 | 364 | 649 |
| $SA_{geo}/V_{geo}$ [mm$^{-1}$] | 0.99 | 1.47 | 1.42 | 1.39 | 1.37 | 1.52 | 1.45 | 0.78 |
| % ($SA_{geo}/V_{geo}$) ** | 100% | 149% | 144% | 141% | 138% | 154% | 147% | 79% |
| pressure drop [Pa · m$^{-1}$] *** | 5,292 | 5,275 | 4,440 | 4,352 | 4,120 | 3,711 | 3,998 | 3,614 |
| Relative pressure drop in comparison to 1-1 [%] | 100% | 99.7% | 83.9% | 82.2% | 77.8% | 70.1% | 75.5% | 68.3% |

* reference example
** based on the ratio of $SA_{geo}/V_{geo}$ of example 1-1
*** at 2.0 m/s, Re = 5,221

The shaped catalyst body 1-2* with a 7-hole cylinder structure and the shaped catalyst bodies 1-3, 1-4, 1-5, 1-6, 1-7 with a tetralobal structure have favorable quotients of the geometric surface of the shaped catalyst body $SA_{geo}$ over the geometric volume of the shaped catalyst body $V_{geo}$ in comparison to 1-1* and 1-8*. The shaped catalyst bodies 1-3, 1-4, 1-5, 1-6, 1-7 and 1-8 with a tetralobal structure induce a significantly lower pressure drop in comparison to the shaped catalyst bodies 1-1* and 1-2*.

Example 2—Preparing Shaped Catalyst Bodies

Shaped catalyst bodies according to Tables 3 and 4 below were prepared by impregnating the refractory supports disclosed in Table 1 with a silver impregnation solution. The supports were obtained from EXACER s.r.l. (Via Puglia 2/4, 41049 Sassuolo (MO), Italy), under Lot-Numbers provided above.

TABLE 3

Catalyst composition (Ag-contents are reported in percent by weight of total catalyst, dopant values are reported in parts per million by weight of total catalyst)

| Example | Support | $Ag_{CAT}$ [wt-%] | $Li_{CAT}$ [ppm] | $S_{CAT}$ [ppm] | $W_{CAT}$ [ppm] | $Cs_{CAT}$ [ppm] | $Re_{CAT}$ [ppm] | $K_{ADD}$ *** [ppm] | $K_{CAT}$ **** [ppm] |
|---|---|---|---|---|---|---|---|---|---|
| 2.2 | A | 15.2 */14.7 ** | 190 | 14 | 200 | 425 | 450 | 51 | 102 |
| 2.3 | B | 29.1 */26.8 ** | 486 | 36 | 556 | 979 | 1190 | 99 | 229 |
| 2.4 | D | 30.9 */29.3 ** | 470 | 35 | 540 | 950 | 1150 | 105 | 232 |
| 2.5 | Q | 29.1 */28.3 ** | 482 | 36 | 551 | 973 | 1178 | 100 | 205 |

* calculated Ag values,
** analyzed Ag values; all promoter values are calculated values;
*** $K_{ADD}$ is understood to mean the amount of potassium added during impregnation and does not include the amount of potassium comprised in the alumina support prior to impregnation;
**** $K_{CAT}$ is understood to mean the total amount of potassium in the catalyst

TABLE 4

Physical Properties of Catalysts

| | Catalyst | | | |
|---|---|---|---|---|
| | 2.2 comparative | 2.3 comparative | 2.4 inventive | 2.5 inventive |
| Carrier | A | B | D | Q |
| Carrier Shape | hollow cylinder | hollow cylinder | tetralobe | tetralobe |
| Number of holes in the carrier | 1 | 1 | 5 | 5 |
| Physical Properties | | | | |
| BET surface area [m$^2$/g] | 0.95 | 2.4 | 2.4 | 2.5 |
| Total Hg pore volume [ml/g] | 0.34 | 0.35 | 0.33 | 0.39 |
| 1$^{st}$ log diff peak [μm] | 1.7 | 0.7 | 0.7 | 0.6 |
| 2$^{nd}$ log diff peak [μm] | 40 | 15 | 17 | 255 |
| Percentage of pores 0.1 to 3 μm in relation to the total Hg pore volume [%] | 45 | 62 | 58 | 52 |
| Catalyst density in 39 mm tube [g/L] | 826 | 876 | 838 | 906 |
| Ag density in 39 mm tube [g/L] | 126 * | 255 * | 259 * | 264 * |
| | 121 ** | 235 ** | 246 ** | 256 ** |
| Side crush strength [N] | | | | |
| along longest diagonal | n.d. *** | 97 | 80 | 108 |
| along side | | | 114 | 142 |

\* calculated values
\*\* analyzed values
\*\*\* n.d. = not determined

2.1 Production of the Silver Complex Solution 783 kg of an aqueous ethylenediamine solution with an ethylenediamine content of 59 wt.-% were pumped into a stirring reactor 1. Subsequently, the ethylenediamine solution was diluted under stirring with 94 kg of deionized water. Next, 26.6 kg of 0.95 wt.-% KOH solution were added to form an aqueous KOH/ethylenediamine solution. The solution was cooled to a temperature of below 20° C. Then 300 kg of oxalic acid dihydrate (purity 99.6%) were added into the stirring reactor 1 stepwise over a period of about 180 minutes under stirring and cooling to control the reaction temperature in the range of 20 to 25° C. Once the addition of oxalic acid dihydrate was completed and the temperature profile from the addition of the last portion of oxalic acid dihydrate passed a maximum, cooling was terminated and the reaction mixture was stirred further for the next 60 min to form an aqueous oxalic acid/ethylenediamine solution.

Next, 1113 kg of the aqueous oxalic acid/ethylenediamine solution were transferred from the stirring reactor 1 to a stirring reactor 2. The reaction medium was cooled to a temperature below 20° C. Then, 500 kg silver oxide powder (from Ames Goldsmith, chemical composition shown below), was added over a period of 225 min under stirring and cooling to control the reaction temperature in the range of 20 to 25° C. Once the addition of silver oxide was completed, and the temperature profile from the addition of the last portion of silver oxide passed a maximum, cooling was terminated and the reaction mixture was heated under stirring in a temperature range of about 25-30° C. for the next 3 hours to form an aqueous Ag complex suspension.

The silver oxide used is commercially available from Ames Goldsmith. Its chemical composition is described below:

| | |
|---|---|
| Silver Content as Ag$_2$O | ≥99.90% |
| moisture content | ≤0.20% |
| chlorides | ≤15 ppm |
| nitrates | ≤100 ppm |
| carbonates | ≤0.25% |
| sulfates | ≤20 ppm |
| copper | ≤20 ppm |
| iron | ≤20 ppm |
| lead | ≤20 ppm |
| nickel | ≤20 ppm |
| sodium | ≤50 ppm |
| other trace metals | ≤20 ppm |

Subsequently, the silver impregnation solution was obtained by passing the reaction mixture through a filtration unit SUPRAdisc® II KS 100 Depth Filter Modules available from Pall Corporation, Port Washington, USA, to remove a minor amount of undissolved solid. The resulting silver impregnation solution had a density of 1.530 g/mL and a silver content of 29.5 wt.-%.

2.2. Preparation of Catalyst Based on Comparative Support A 174.3 g of support A listed in Table 1 was placed into a 2 L glass flask. The flask was attached to a rotary evaporator which was set under vacuum pressure of 80 mbar. The rotary evaporator system was set in rotation of 30 rpm. 105.98 g of the silver complex solution prepared according to Example 2.1 was mixed with 1.3722 g of promoter solution I, 2.0583 g of promoter solution II, and 2.5033 g of promoter solution III. Promoter solution I was made from dissolving lithium nitrate (FMC, 99.3%) and ammonium sulfate (Merck, 99.4%) in DI water to achieve Li content of 2.85 wt.-% and S content of 0.21 wt.-%. Promoter solution II was made from dissolving tungstic acid (HC Starck, 99.99%) in DI water and cesium hydroxide in water (HC Starck, 50.42%) to achieve target Cs content of 4.25 wt.-% and W content of 2.0 wt.-%. Promoter solution III was made from dissolving ammonium perrhenate (Engelhard, 99.4%) in DI water to achieve Re content of 3.7 wt.-%. The combined impregnation solution containing silver complex solution, promoter solutions I, II, and III was stirred for 5 minutes. The combined impregnation solution was added onto the support A over 15 minutes under vacuum of 80 mbar. After addition of the combined impregnation solution, the rotary evaporator system was continued to rotate under vacuum for another 15 minutes. The impregnated support was then left in the apparatus at room temperature and atmospheric pressure for 1 hour and mixed gently every 15 minutes. The impregnated material was calcined for 10 minutes at 290° C. under 23 m3/h flowing nitrogen in a calcination oven to yield the final catalyst 2.2.

2.3. Preparation of Catalyst Based on Comparative Support B.

Step 2.3.1. Preparation of Ag-Containing Intermediate 585 kg of a commercially available alpha-alumina support B listed in Table 1 were placed in a vacuum tumble mixer having a volume of 1.8 $m^3$. The support was impregnated with 468 kg of Ag complex solution prepared according to Example 2.1 under a reduced pressure of 50 mbar and at a rate of rotation of 0.5 revolutions/min. Impregnation was carried out at room temperature over a period of 4 hours. The vacuum was then broken and the impregnated support was transferred to a belt calciner. The impregnated material was further heated on a belt calciner at a temperature of 290° C. in nitrogen flow according to calcination parameters described in WO2012/140614 to form a Ag-containing intermediate product.

Step 2.3.2. Preparation of Final Catalyst 328 kg of Ag complex solution prepared according to Example 2.1 were mixed with 13.23 kg of promoter solution I containing Li and S, 14.37 kg of promoter solution II containing Cs and W, and 24.93 kg of promoter solution III containing Re to form Ag impregnation solution.

The promoter solution I was prepared by dissolving $LiNO_3$ and $(NH_4)_2SO_4$ in water to form a solution with Li-content of 2.85 wt.-% and S-content of 0.21 wt.-%. The promoter solution II was prepared by dissolving CsOH and $H_2WO_4$ in water to form a solution with Cs-content of 5.3 wt.-% and W-content of 3.0 wt.-%. The promoter solution III was prepared by dissolving $NH_4ReO_4$ in water to form a solution with Re-content of 3.7 wt.-%.

634 kg of Ag-containing intermediate prepared according to Step 2.3.1 were impregnated with 357 kg of the Ag impregnation solution under a reduced pressure of 50 mbar and at a rate of rotation of 0.5 revolutions/min. Impregnation was carried out at room temperature over a period of 3 hours. The vacuum was then broken and the impregnated support was transferred to a belt calciner. The impregnated material was further heated on a belt calciner at a temperature of 290° C. in nitrogen flow according to calcination parameters described in WO2012/140614 to form a final ethylene oxide catalyst 2.3.

2.4. Preparation of Catalyst Based on Support D.

Step 2.4.1. Preparation of Ag-Containing Intermediate 174 g of support D listed in Table 1 was placed into a 2 L glass flask. The flask was attached to a rotary evaporator which was set under vacuum pressure of 80 mbar. The rotary evaporator system was set in rotation of 30 rpm. 149.2 of silver complex solution prepared according to Example 2.1 was added onto support D over 15 minutes under vacuum of 30 mbar. After addition of the silver complex solution, the rotary evaporator system was continued to rotate under vacuum for another 15 minutes. The impregnated support was then left in the apparatus at room temperature and atmospheric pressure for 1 hour and mixed gently every 15 minutes. The impregnated support was calcined for 12 minutes at 290° C. under 23 $m^3$/h flowing nitrogen in a calcination oven to yield Ag-containing intermediate product.

Step 2.4.2. Preparation of Final Catalyst 2.1 with Properties Listed in Tables 3 and 4.

213 g of Ag-containing intermediate product prepared according to step 2.4.1 were placed into a 2 L glass flask. The flask was attached to a rotary evaporator which was set under vacuum pressure of 80 mbar. The rotary evaporator system was set in rotation of 30 rpm. 112.52 g of the silver complex solution prepared according to step 3.1 was mixed with 4.0728 g of promoter solution I, 4.4454 g of promoter solution II, and 7.6761 g of promoter solution III. Promoter solution I was made from dissolving lithium nitrate (FMC, 99.3%) and ammonium sulfate (Merck, 99.4%) in DI water to achieve Li content of 2.85 wt.-% and S content of 0.21 wt.-%. Promoter solution II was made from dissolving tungstic acid (HC Starck, 99.99%) in DI water and cesium hydroxide in water (HC Starck, 50.42%) to achieve target Cs content of 5.28 wt.-% and W content of 3.0 wt.-%. Promoter solution III was made from dissolving ammonium perrhenate (Engelhard, 99.4%) in DI water to achieve Re content of 3.7 wt.-%. The combined impregnation solution containing silver complex solution, promoter solutions I, II, and III was stirred for 5 minutes. The combined impregnation solution was added onto the silver-containing intermediate product 2.4.1 over 15 minutes under vacuum of 80 mbar. After addition of the combined impregnation solution, the rotary evaporator system was continued to rotate under vacuum for another 15 minutes. The impregnated support was then left in the apparatus at room temperature and atmospheric pressure for 1 hour and mixed gently every 15 minutes. The impregnated material was calcined for 10 minutes at 290° C. under 23 $m^3$/h flowing nitrogen in a calcination oven to yield the final catalyst 2.4.

2.5. Preparation of Catalyst Based on Support Q.

Catalyst 2.5, having the chemical composition and properties listed in Tables 3 and 4, was prepared according to steps 2.3.1 and 2.3.2, wherein Comparative Support B was replaced with inventive Support Q, and the amount of the promoter solutions was adjusted to obtain the target composition as shown in Table 3.

Example 3—Catalyst Testing 3.1. Testing of Crushed Catalysts with Different Particle Sizes in a Mini Plant.

The epoxidation reaction was conducted in a vertically-placed test reactor constructed from stainless steel with an inner-diameter of 6 mm and a length of 2.2 m. The reactor was heated using hot oil contained in a heating mantel at a specified temperature. All temperatures below refer to the temperature of the hot oil. The reactor was filled with 29 g of inert steatite balls (1.0-1.6 mm), then packed with a desired amount of crushed catalyst screened to a desired particle size and then again packed with additional 9 g of inert steatite balls (1.0-1.6 mm). The inlet gas was introduced to the top of the reactor in a "once-through" operation mode.

Catalyst 2.2.a and catalyst 2.3.a were screened to a particle size of 0.5-0.9 mm. Catalyst 2.2.b and catalyst 2.3.b were screened to a particle size of 2-3.15 mm. The filling amount of the catalysts 2.2.a and 2.2.b was 34.9 g. The filling volume of the catalyst 2.2.a was 31.1 ml. The filling volume of the catalyst 2.2.b was 43.9 ml. The filling amount of the catalysts 2.3.a and 2.3.b was 33.5 g. The filling volume of the catalyst 2.3.a was 31.1 ml. The filling volume of the catalyst 2.3.b was 39.3 ml.

The catalysts were conditioned in the inlet gas consisted of 20 vol % ethylene, 4 vol % oxygen, 1 vol % $CO_2$, and ethylene chloride (EC) moderation of 2.5 parts per million by volume (ppmv), with methane used as a balance at the total gas flow rate of 152.7 Nl/h, a pressure of about 15 bar. The conditioning temperature during tests o catalysts 2.2.a and 2.2.b was 250° C. with duration of 61 hours. The conditioning temperature during tests of catalysts 2.3.a and 2.3.b was 245° C. with duration of 108 hours.

The temperature during evaluation of catalysts 2.2.a and 2.2.b. was decreased after the conditioning phase to 235° C., while maintaining the EC concentration at 2.5 ppmv. The temperature during evaluation of catalysts 2.3.a and 2.3.b. was decreased after the conditioning phase to 225° C., the EC concentration was decreased to 1.5 ppmv.

Then, for all tested catalysts, the inlet gas composition was gradually changed to 35 vol % ethylene, 7 vol % oxygen, 1 vol % $CO_2$ with methane used as a balance and the total gas flow rate of 147.9 Nl/h. The temperature during tests was adjusted to achieve comparable ethylene oxide (EO) concentrations in the outlet gas for selected couple of catalysts (2.2.a/2.2.b or 2.3.a/2.3.b). At every selected condition, the EC concentration was adjusted to optimize the selectivity.

Results of the catalyst tests are shown in Table 5.

TABLE 5

Test Reaction Results

| catalyst | particle size [mm] | catalyst volume [mL] | EO outlet concentration [vol-%] | EO selectivity [%] | temperature [° C.] | time on stream incl. condition phase [d] | work rate [$kg_{EO}/(m^3_{cat}h)$] |
|---|---|---|---|---|---|---|---|
| 2.2.a | 0.5-0.9 | 31.1 | 2.73 | 91.3 | 245 | 13 | 250 |
| 2.2.b | 2.0-3.15 | 43.9 | 2.73 | 91.0 | 243 | 13 | 178 |
| 2.2.a | 0.5-0.9 | 31.1 | 2.0 | 91.6 | 238 | 21 | 180 |
| 2.2.b | 2.0-3.15 | 43.9 | 2.0 | 91.4 | 237 | 21 | 128 |
| 2.2.a | 0.5-0.9 | 31.1 | 3.07 | 90.9 | 250 | 27 | 280 |
| 2.2.b | 2.0-3.15 | 43.9 | 3.07 | 90.9 | 247 | 27 | 198 |
| 2.3.a | 0.5-0.9 | 31.1 | 3.04 | 89.9 | 232 | 41 | 280 |
| 2.3.b | 2.0-3.15 | 39.3 | 3.04 | 89.3 | 235 | 41 | 222 |

The test results show that for the catalysts 2.2.a/2.2.b with a Ag-content of 15 wt.-% and a BET surface area of 0.95 $m^2/g$ within the tested range of comparable EO outlet concentrations of 2.0-3.07 vol-%, the difference in selectivity is ≤0.3%. On the other hand, for the catalysts 2.3.a/2.3.b with a Ag-content of 29 wt.-% and a BET surface area of 2.4 $m^2/g$ the difference in selectivity is 0.6%. Therefore, the increase of particle size has a more pronounced negative effect on the catalysts with a Ag-content of 29 wt.-% and a BET surface area of 2.4 $m^2/g$.

3.2. Testing of Catalyst Bodies in a Pilot Plant.

The epoxidation reaction was conducted in a vertically-placed test reactor constructed from stainless steel with an inner-diameter of 44 mm and a length of 12.80 m. The reactor was equipped with a thermocouple of an outer diameter of 8 mm positioned in the center of the reactor. Reactor temperature was regulated using pressurized water contained in the reactor mantel. Catalyst temperatures were measured using the thermocouple at five different positions equally distributed along the reactor length. All temperatures below refer to an average catalyst temperature of the five measurements. Catalyst bodies (14.5 kg of Comparative Catalyst 2.3 in a first test, and 16.3 kg of Inventive Catalyst 2.5 in a second test) were charged into the reactor so as to provide a catalyst bed with a height of 11.9 m. 0.65 m of inert ceramic balls were packed on top of the catalyst bed.

The catalysts were conditioned in a mixture of 55 to 60 $Nm^3/h$ of reaction gas and 25 to 30 $Nm^3/h$ of nitrogen at an average catalyst temperature of 255 to 260° C. and a reactor outlet pressure of about 15 bar for about 36 hours. The reaction gas contained 35 to 40 vol.-% of ethylene, 6.5 to 7.5 vol.-% of oxygen, 0.4 to 0.8 vol.-% of carbon dioxide, 0.5 to 4 vol.-% of nitrogen, 0.1 to 0.3 vol.-% of ethane, 0.15 to 0.25 vol.-% of water, about 1 ppm of vinyl chloride, and methane as a balance gas. Additionally, 1.7 to 2.0 ppm of ethyl chloride were dosed into the feed during conditioning.

Subsequently, the catalyst temperature was decreased to about 235 to 240° C., the nitrogen flow was gradually decreased to 0 $Nm^3/h$, and the reaction gas flow was gradually increased to adjust the GHSV to 4800 $h^{-1}$. Then, the temperature was adjusted to control a work rate at 280 $kg(EO)/m^3(cat)h$ or an EO outlet concentration of 2.97 vol %. The concentration of chlorine-containing components (ethyl chloride, vinyl chloride and methyl chloride) was optimized to achieve the highest possible selectivity.

Results of the catalyst tests are shown in Table 6.

TABLE 6

Test Reaction Results

| | | Example | |
|---|---|---|---|
| | | 2.3 Comparative | 2.5 Inventive |
| | | Shape | |
| | | Ring | Tetralobe Passageways |
| cumulative EO production | Performance | 1 | 5 |
| 100 t(EO)/$m^3$(cat) | Catalyst temperature [° C.] | 243 | 232 |
| | Selectivity [%] | 86.0 | 87.5 |
| 300 t(EO)/$m^3$(cat) | Catalyst temperature [° C.] | 245 | 235 |
| | Selectivity [%] | 87.6 | 89.1 |
| 500 t(EO)/$m^3$(cat) | Catalyst temperature [° C.] | 245 | 237 |
| | Selectivity [%] | 87.4 | 89.1 |
| 700 t(EO)/$m^3$(cat) | Catalyst temperature [° C.] | 245 | 239 |
| | Selectivity [%] | 87.5 | 89.7 |

TABLE 6-continued

Test Reaction Results

| | | Example | |
|---|---|---|---|
| | | 2.3 Comparative Shape | 2.5 Inventive Shape |
| | | Ring | Tetralobe Passageways |
| cumulative EO production | Performance | 1 | 5 |
| 900 t(EO)/m³(cat) | Catalyst temperature [° C.] | 247 | 240 |
| | Selectivity [%] | 87.5 | 90.0 |

The test results show that the catalyst temperature is lower and the selectivity is higher for catalyst 2.5 than for catalyst 2.3 at all production rates.

The invention claimed is:

1. A process for producing ethylene oxide by gas-phase oxidation of ethylene, comprising:
   directing a feed comprising gaseous ethylene and gaseous oxygen through a packing of individual shaped catalyst bodies, under conditions conducive to obtain a reaction mixture containing at least 2.7 vol. % of ethylene oxide, comprising a catalyst temperature in the range of 150 to 350° C. and at a pressure in the range of 5 to 30 bar absolute;
   wherein each shaped catalyst body comprises silver deposited on a refractory support and is characterized by
   a content of at least 20 wt. % of silver, relative to the total weight of the shaped catalyst body;
   a BET surface area in the range of 1.6 to 3.0 m²/g;
   a first face side surface, a second face side surface and a circumferential surface with a plurality of passageways extending from the first face side surface to the second face side surface; and
   a uniform multilobed cross-section; and
   a longest direct diffusion pathway d, with 2d being in the range of 0.7 to 2.4 mm, wherein the longest diffusion pathway d is defined as the shortest distance from the geometric surface of the shaped catalyst body to a point inside the structure of the shaped catalyst body for which point the shortest distance is the largest among all points.

2. The process according to claim 1, wherein the packing of the shaped catalyst body has a packed silver density of at least 140 g/L, wherein the packed silver density is the silver density per liter of a tubular reactor with the shaped catalyst body, as measured in a reactor tube with an inner diameter of 39 mm.

3. The process according to claim 1, wherein the concentration of carbon dioxide in the feed is at most 3 vol-% of carbon dioxide, relative to the total volume of the feed.

4. The process according to claim 1, wherein the process is carried out to achieve an EO-space-time-yield of greater than 250 $kg_{EO}/(m^3_{cat}h)$.

5. The process according to claim 1, wherein the shaped catalyst body has a total Hg pore volume of 0.2 mL/g to 0.6 mL/g, as determined by Hg intrusion measurements.

6. The process according to claim 5, wherein the catalyst has a multimodal pore size distribution with a first pore size distribution maximum in the range of 0.1 to 3.0 μm and a second pore size distribution maximum in the range of 8.0 to 100 μm, wherein at least 40% of the total Hg pore volume of the shaped catalyst body stems from pores with a diameter in the range of 0.1 to 3.0 μm.

7. The process according to claim 1, wherein the cross-section of the multilobed body has a quotient of the diameter of the inscribed circle over the diameter of the circumscribed circle is at most 0.9, wherein the inscribed circle is the largest possible circle that can be drawn inside the multilobe cross-section, and the circumscribed circle is the smallest circle that completely contains the multilobe cross-section within it.

8. The process according to claim 1, wherein the shaped catalyst body comprises a plurality of outer passageways being arranged around a central passageway with one outer passageway being assigned to each lobe, wherein neighboring outer passageways are arranged essentially equidistantly to each other and the outer passageways are arranged essentially equidistantly to the central passageway.

9. The process according to claim 1, wherein the multilobed body is a tetralobed body comprising a central passageway.

10. The process according to claim 9, wherein the central passageway has a cross-sectional area $a_1$ and the outer passageways each have a cross-sectional area $a_2$, and the ratio of $a_1$ to $a_2$ is in the range of 0.15 to 1.0.

11. The process according to claim 1, wherein the shaped catalyst body comprises 400 to 2000 ppm by weight of rhenium, relative to the total weight of the shaped catalyst body.

12. The process according to claim 1, wherein the shaped catalyst body comprises 260 to 1750 ppm by weight of cesium, relative to the total weight of the shaped catalyst body.

13. The process according to claim 1, wherein the refractory support is an aluminum oxide support.

14. The process according to claim 1, wherein the packing of the shaped catalyst body has a packed silver density of at least 180 g/L, wherein the packed silver density is the silver density per liter of a tubular reactor with the shaped catalyst body, as measured in a reactor tube with an inner diameter of 39 mm.

* * * * *